United States Patent
Sasaki et al.

(10) Patent No.: US 7,251,981 B2
(45) Date of Patent: Aug. 7, 2007

(54) METHOD AND DEVICE FOR DIAGNOSING GAS SENSOR DEGRADATION

(75) Inventors: Takashi Sasaki, Shioya-gun (JP);
Hiroyuki Abe, Utsunomiya (JP);
Tsuyoshi Eguchi, Utsunomiya (JP);
Yasushi Kojima, Utsunomiya (JP);
Takashi Saito, Shioya-gun (JP);
Akihiro Suzuki, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 65 days.

(21) Appl. No.: 10/514,254

(22) PCT Filed: May 12, 2003

(86) PCT No.: PCT/JP03/05897

§ 371 (c)(1),
(2), (4) Date: Nov. 12, 2004

(87) PCT Pub. No.: WO03/096000

PCT Pub. Date: Nov. 20, 2003

(65) Prior Publication Data

US 2005/0155405 A1   Jul. 21, 2005

(30) Foreign Application Priority Data

May 13, 2002   (JP)   ............................. 2002-137649
Dec. 25, 2002   (JP)   ............................. 2002-374086
Mar. 14, 2003   (JP)   ............................. 2003-070227

(51) Int. Cl.
*G01N 7/00* (2006.01)

(52) U.S. Cl. .................................................... 73/23.21

(58) Field of Classification Search ................ 73/23.21
See application file for complete search history.

(56) References Cited

U.S. PATENT DOCUMENTS 6,673,480 B1 *   1/2004   Wilkinson et al. ............ 429/13
6,905,998 B2 *   6/2005   Naka et al. ................... 502/38
2004/0005494 A1 *   1/2004   Drake et al. .................. 429/38

FOREIGN PATENT DOCUMENTS

EP   0 751 390 A2   1/1997
JP   61-239153   10/1986

(Continued)

Primary Examiner—Michael Cygan
(74) Attorney, Agent, or Firm—Lahive & Cockfield, LLP; Anthony A. Laurentano, Esq.

(57) ABSTRACT

A degradation diagnosis method for simply performing degradation diagnosis of a gas sensor such as a hydrogen sensor. The hydrogen sensor has a reference detector member and common detector member, with each detector member respectively constituted of a detector element and temperature compensating element that form a pair. Power is normally supplied to the common detector member, which performs concentration detection of the hydrogen gas. When performing degradation diagnosis of this common detector member, concentration detection is performed simultaneously by each detector member for the gas of the prescribed hydrogen concentration by supplying power to both the common detector member and reference detector member and comparing the output value of the common detector member and the output value of the reference detector member.

24 Claims, 24 Drawing Sheets

FOREIGN PATENT DOCUMENTS

| | | |
|---|---|---|
| JP | 64-089155 | 4/1989 |
| JP | 6-11472 | 1/1994 |
| JP | 6-52662 | 7/1994 |
| JP | 6-223850 | 8/1994 |
| JP | 9-15186 | 1/1997 |
| JP | 10-10069 | 1/1998 |
| JP | 10-48171 | 2/1998 |
| JP | 10-170463 | 6/1998 |

\* cited by examiner ns of International Application No. PCT/JP03/05897, filed 12 May 2003, which claims priority to Japanese Patent Application No. 2002-137649 filed on 13 May 2002, Japanese Patent Application No 2002-374086 filed 25 Dec. 2002, and Japanese Patent Application No 2003-070227 filed 14 Mar. 2003, in Japan. The contents of the aforementioned applications are hereby incorporated by reference.

TECHNICAL FIELD

This invention relates to a method and device for diagnosing degradation in gas sensors such as hydrogen sensors.

BACKGROUND ART

A solid polymer membrane fuel cell, for instance, has a stack comprised by stacking a plurality of cells formed by sandwiching a solid polymer electrolyte membrane from both sides by an anode and a cathode, with hydrogen fed to the anode as fuel, and air fed to the cathode as an oxidant. Hydrogen ions generated at the anode by a catalytic reaction move through the solid polymer electrolyte membrane to the cathode, where they cause an electrochemical reaction with oxygen to generate electricity.

In fuel cells such as this kind of solid polymer membrane fuel cell, unreacted air discharged from the cathode (referred to as air off-gas) is normally discharged out of the system, in which case the hydrogen gas concentration in the air off-gas must be confirmed.

Systems have been developed in the past for confirming the concentration of hydrogen gas in air off-gas by, for example, installing a hydrogen detector in the discharge system of the cathode side of the fuel cell (see, for example, Japanese Examined Patent Application, Second Publication No. H06-52662).

A protective device is also known that shuts off the fuel supply when hydrogen at the fuel electrode side is detected to have leaked through the solid polymer electrolyte membrane to the oxygen electrode side by means of, for example, a gas sensor for detecting hydrogen gas provided in the discharge system of the oxygen electrode side of the fuel cell (see, for example, Japanese Unexamined Patent Application, First Publication No. H06-223850).

Use of a gas contact combustion-type gas detector is being considered in these hydrogen detectors. This gas contact combustion-type gas sensor comprises a detector element to which a catalyst is attached and a temperature compensating element to which a catalyst is not attached. Utilizing the heat of combustion when the detected gas (hydrogen in the case of a hydrogen detector) contacts the catalyst, it detects the gas concentration of the detected gas from the difference in electrical resistance between the detector element and the temperature compensating element.

Meanwhile, silicon in materials such as sealant used in a fuel cell can mix with the air off-gas, and when the hydrogen detector is exposed to this silicon during the catalytic reaction, the catalyst is poisoned. As a result, the hydrogen detector is degraded, and the detection accuracy drops. In addition, along with this silicon poisoning, degradation such as a drop in sensitivity due to sulfur poisoning and water absorption and the like may occur. Depending on the extent of degradation, replacement of the hydrogen detector may be required.

Accordingly, degradation diagnosis for hydrogen detectors is extremely important, and a method to easily diagnose whether a hydrogen detector is degraded or not is anxiously awaited.

SUMMARY OF THE INVENTION

The present invention was achieved in view of the above circumstances and has as its object the provision of a gas sensor degradation diagnosis method and gas sensor degradation diagnosis device capable of easily diagnosing gas sensor degradation.

In order to solve the abovementioned problem and achieve the above-mentioned object, the present invention provides a gas sensor degradation diagnosis method for diagnosing the degradation of a detection means employing a plurality of detector members that include detector elements and temperature compensating elements and that are disposed in close proximity to one another, with at least one of the plurality of detector members serving as a reference detector member, and the others serving as common detector members, the gas sensor degradation diagnosis method including the steps of: performing concentration detection of the gas under detection by the common detector members by supplying power to the common detector members during concentration detection of the gas under detection; performing concentration detection of the gas under detection by means of each of the detector members by supplying power to both the common detector members and the reference detector members during degradation diagnosis of the common detector members; and performing degradation diagnosis of the common detector members by comparing the output values of the common detector members with the output values of the reference detector members.

According to the aforementioned gas sensor degradation diagnosis method, degradation of the reference detector members can be inhibited compared to the common detector members by performing concentration detection of the gas under detection by supplying power to the common detector members, for example by cutting power to the reference detector members. During degradation diagnosis of the common detector members, diagnosis (relative diagnosis) of whether the common detector members are degraded or not can be easily performed by supplying power to both the common detector members and the reference detector members and relatively comparing the output values of the common detector members and the output values of the reference detector members.

Furthermore, in the gas sensor degradation diagnosis method of the present invention, the plurality of detector members may be mutually positioned in close proximity so that substantial differences in the concentration detection results for the gas under detection obtained by each detector member are within the prescribed range.

According to the aforementioned gas sensor degradation diagnosis method, when for example feeding gas under detection of an equivalent gas concentration to a plurality of detector members, even if the detection result of each detector member differs in accordance with the arrangement position of each detector member, a lowering of the diagnostic accuracy of the degradation diagnosis of the common detector members by relative diagnosis can be restricted.

Furthermore, in the gas sensor degradation diagnosis method of the present invention, the aforementioned prescribed range may be set to within ±10% with respect to the detection result.

According to the aforementioned gas sensor degradation diagnosis method, a lowering of the diagnostic accuracy of the degradation diagnosis of the common detector members by relative diagnosis can be further restricted.

Furthermore, in the gas sensor degradation diagnosis method of the present invention, the gas concentration of the gas under detection may be set to an arbitrary concentration detectable by at least the common detector members when performing degradation diagnosis of the common detector members.

According to the aforementioned gas sensor degradation diagnosis method, during degradation diagnosis of the common detector members, concentration detection of the gas to be detected is performed by each detector member simultaneously by supplying power to both the common detector members and reference detector members and relatively comparing them, so there is no necessity for the gas concentration of the gas to be detected to be a known value, and the gas to be detected of the same gas concentration may be supplied to the common detector members and reference detector members.

Herewith, degradation diagnosis of the common detector members is possible even when the gas concentration of the gas to be detected during degradation diagnosis is not constant and fluctuates.

Furthermore, in the gas sensor degradation diagnosis method of the present invention, the gas sensor may be judged as degraded when the result of comparing the output values of the common detector members with the output values of the reference detector members is outside the prescribe range.

According to the aforementioned gas sensor degradation diagnosis method, it can be determined with certainty whether or not the common detector members are degraded. The comparison values may be the difference between the output values of the common detector members and the output values of the reference detector members, and may be the quotient obtained by dividing either one of the output values of the common detector members with the output values of the reference detector members by the other.

Furthermore, in the gas sensor degradation diagnosis method of the present invention, the comparison result is the difference between the output values of the common detector members and the output values of the reference detector members, or the ratio of either one of the output values of the common detector members and the output values of the reference detector members to the other.

According to the aforementioned gas sensor degradation diagnosis method, it can be easily determined whether the common detector members are degraded.

Furthermore, in the gas sensor degradation diagnosis method of the present invention, the prescribed range is the prescribed region set in advance according to the output values of the common detector members and the output values of the reference detector members, and the gas sensor may be judged as degraded when the output values of the common detector members are greater than the maximum values of the prescribed region corresponding to the output values of the reference detector members, or smaller than the minimum values of the prescribed region corresponding to the output values of the reference detector members.

According to the aforementioned gas sensor degradation diagnosis method, it can be easily determined whether the common detector members are degraded.

Furthermore, in the gas sensor degradation diagnosis method of the present invention, the degradation diagnosis of the reference detector members may be performed based on the output values of the reference detector members when the gas under detection is detected by the reference detector members.

According to the aforementioned gas sensor degradation diagnosis method, the degradation diagnosis of the reference detector members serving as the reference when relatively diagnosing the degradation diagnosis of the common detector members can be somewhat absolutely diagnosed by the output values of the reference detector members. This can improve the diagnostic accuracy of degradation diagnosis for common detector members by relative analysis.

Furthermore, in the gas sensor degradation diagnosis method of the present invention, the gas under detection may have a known concentration.

According to the aforementioned gas sensor degradation diagnosis method, it is possible to diagnose absolutely whether the reference detector members are degraded or not by the gas under detection having a known concentration, and the diagnosis accuracy of the degradation diagnosis for common detector members by relative diagnosis can be further improved.

Furthermore, in the gas sensor degradation diagnosis method of the present invention, the dilute gas, which is obtained by diluting the fuel gas discharged from the fuel cell that generates electricity by electrochemical reaction from supplied fuel gas and oxidant gas with the oxidant gas discharged from the fuel cell, is mixed with the oxidant gas discharged from the fuel cell and may serve as the gas under detection of the known concentration.

According to the aforementioned gas sensor degradation diagnosis method, degradation diagnosis of the reference detector members can be carried out by effective utilization of the fuel gas output from the fuel cell.

Furthermore, in the gas sensor degradation diagnosis method of the present invention, the gas under detection of the required concentration may be mixed with the ambient gas of the reference detector members to serve as the gas under detection of the known concentration.

According to the aforementioned gas sensor degradation diagnosis method, degradation diagnosis can be easily performed with the reference detector members in the mounted state without, for example, removing the reference detector members from the mounted position.

Furthermore, in the gas sensor degradation diagnosis method of the present invention, degradation diagnosis of the reference detector members may be performed at less frequency than the frequency of performing degradation diagnosis of the common detector members.

According to the aforementioned gas sensor degradation diagnosis method, by restricting increases in the frequency of supplying power to the reference detector members, degradation of the reference detector members is inhibited and reductions in the diagnosis accuracy of the degradation diagnosis of the common detector members by relative diagnosis can be restricted.

Furthermore, in the gas sensor degradation diagnosis method of the present invention, the detection means may be a gas contact combustion-type gas sensor that detects the gas concentration of the gas under detection based on the difference in the electrical resistance values between the detector element and the temperature compensating element generated in accordance with the combustion of the gas under detection that comes into contact with the catalyst of the detector element.

According to the aforementioned gas sensor degradation diagnosis method, degradation diagnosis can be easily performed even for degradation of the gas sensor stemming from deactivation of the catalyst of the detector element by a deactive material.

Furthermore, in the gas sensor degradation diagnosis method of the present invention, the gas under detection is hydrogen gas, and the detection means may be a hydrogen sensor that detects the hydrogen gas concentration in oxidant gas discharged from the oxygen electrode of a fuel cell.

According to the aforementioned gas sensor degradation diagnosis method, while accurately grasping the operational status of the fuel cell by a hydrogen sensor, degradation diagnosis of the hydrogen sensor can be easily performed even during operation of the fuel cell.

Furthermore, in the gas sensor degradation diagnosis method of the present invention, the gas under detection may be hydrogen gas, and the detection means may be a hydrogen sensor that detects the hydrogen gas concentration of ambient gas in the interior of a vehicle.

According to the aforementioned gas sensor degradation diagnosis method, while accurately grasping the state of a vehicle and, for example, the operational status of a fuel cell mounted in the vehicle by a hydrogen sensor, degradation diagnosis of the hydrogen sensor can be easily performed even when the vehicle is being operated.

In addition, the gas sensor degradation diagnosis device of the present invention is characterized by including a detection means employing a plurality of detector members that include detector elements and temperature compensating elements and that are disposed in close proximity to one another, with at least one of the plurality of detector members serving as a reference detector member and the others serving as regular detector members; common detection means that performs concentration detection of the gas under detection with the common detector members by supplying power to the common detector members during concentration detection of the gas under detection; relative diagnosis means that performs concentration detection of the gas under detection with each of the detector members by supplying power to both the common detector members and the reference detector members during degradation diagnosis of the common detector members; comparison means that compares the output values of the common detector members with the output values of the reference detector members; and relative judgment means that perform degradation judgment of the common detector members depending on the comparison result of the comparison means.

According to the gas sensor degradation diagnosis device of the aforementioned constitution, degradation of the reference detector members can be inhibited compared to the common detector members by performing concentration detection of the gas under detection by supplying power to the common detector members, for example by cutting power to the reference detector members. During degradation diagnosis of the common detector members, diagnosis of whether the common detector members are degraded or not can be easily performed by supplying power to both the common detector members and the reference detector members and relatively comparing the output values of the common detector members and the output values of the reference detector members.

Furthermore, in the gas sensor degradation diagnosis device of the present invention, the plurality of detector members may be mutually positioned in close proximity so that substantial differences in the concentration detection results for the gas under detection obtained by each detector member are within the prescribed range.

According to the gas sensor degradation diagnosis device of the aforementioned constitution, when for example feeding gas under detection of an equivalent gas concentration to a plurality of detector members, even if the detection result of each detector member differs in accordance with the arrangement position of each detector member, a lowering of the diagnostic accuracy of the degradation diagnosis of the common detector members by relative diagnosis can be restricted.

Furthermore, in the gas sensor degradation diagnosis device of the present invention, the aforementioned prescribed range may be set to within ±10% with respect to the detection result.

According to the gas sensor degradation diagnosis device of the aforementioned constitution, a lowering of the diagnostic accuracy of the degradation diagnosis of the common detector members by relative diagnosis can be further restricted.

Furthermore, the gas sensor degradation diagnosis device of the present invention may have an absolute diagnostic means that performs concentration detection of the gas under detection with the reference detector members by supplying power to the reference detector members during degradation diagnosis of the reference detector members and an absolute determination means that performs degradation determination of the reference detector members based on the output values of the reference detector members.

According to the gas sensor degradation diagnosis device of the aforementioned constitution, the degradation diagnosis of the reference detector members serving as the reference when relatively diagnosing the degradation diagnosis of the common detector members can be somewhat absolutely diagnosed by the output values of the reference detector members. This can improve the diagnostic accuracy of degradation diagnosis for common detector members by relative analysis.

Furthermore, the gas sensor degradation diagnosis device of the present invention may have fuel cell that generates electricity by electrochemical reaction from the supplied fuel gas and oxidant gas, a dilution means that dilutes the fuel gas discharged from the fuel cell with the oxidant gas discharged from the fuel cell, and a means for supplying gas of a known concentration that mixes the dilute gas output from the dilution means with the oxidant gas discharged from the fuel cell to make the gas under detection of a known concentration and supply it to the reference detector members.

According to the gas sensor degradation diagnosis device of the aforementioned constitution, degradation diagnosis of the reference detector members can be carried out by effective utilization of the fuel gas output from the fuel cell.

Furthermore, the gas sensor degradation diagnosis device of the present invention may have a known concentration gas supply means that mixes the gas under detection of the prescribed concentration in ambient gas of the reference detector members to produce the gas under detection of a known concentration and supplies it to the reference detector members.

According to the gas sensor degradation diagnosis device of the aforementioned constitution, degradation diagnosis can be easily performed with the reference detector members in the mounted state without, for example, removing the reference detector members from the mounted position.

Furthermore, in the gas sensor degradation diagnosis device of the present invention, the detection means may be a gas contact combustion-type gas sensor that detects the gas concentration of the gas under detection based on the difference in the electrical resistance values between the detector element and the temperature compensating element generated in accordance with the combustion of the gas under detection that comes into contact with the catalyst of the detector element.

According to the gas sensor degradation diagnosis device of the aforementioned constitution, degradation diagnosis can be easily performed even for degradation of the gas sensor stemming from poisoning of the catalyst of the detector element by a poisoned material.

Furthermore, in the gas sensor degradation diagnosis device of the present invention, the gas under detection is hydrogen gas, and the detection means may be a hydrogen sensor, arranged in the flow of oxidant gas discharged from the oxygen electrode of the fuel cell, that detects the hydrogen gas concentration in the oxidant gas flowing in the path.

According to the gas sensor degradation diagnosis device of the aforementioned constitution, while accurately grasping the operational status of the fuel cell by a hydrogen sensor, degradation diagnosis of the hydrogen sensor can be easily performed even during operation of the fuel cell.

Furthermore, in the gas sensor degradation diagnosis device of the present invention, the gas under detection may be hydrogen gas, and the detection means may be a hydrogen sensor, positioned in the interior of a vehicle, that detects the hydrogen gas concentration of ambient gas in the vehicle interior.

According to the gas sensor degradation diagnosis device of the aforementioned constitution, while accurately grasping the state of a vehicle and, for example, the operational status of a fuel cell mounted in the vehicle by a hydrogen sensor, degradation diagnosis of the hydrogen sensor can be easily performed even when the vehicle is being operated.

DETAILED DESCRIPTION OF THE ILLUSTRATED EMBODIMENT

Figure 1:
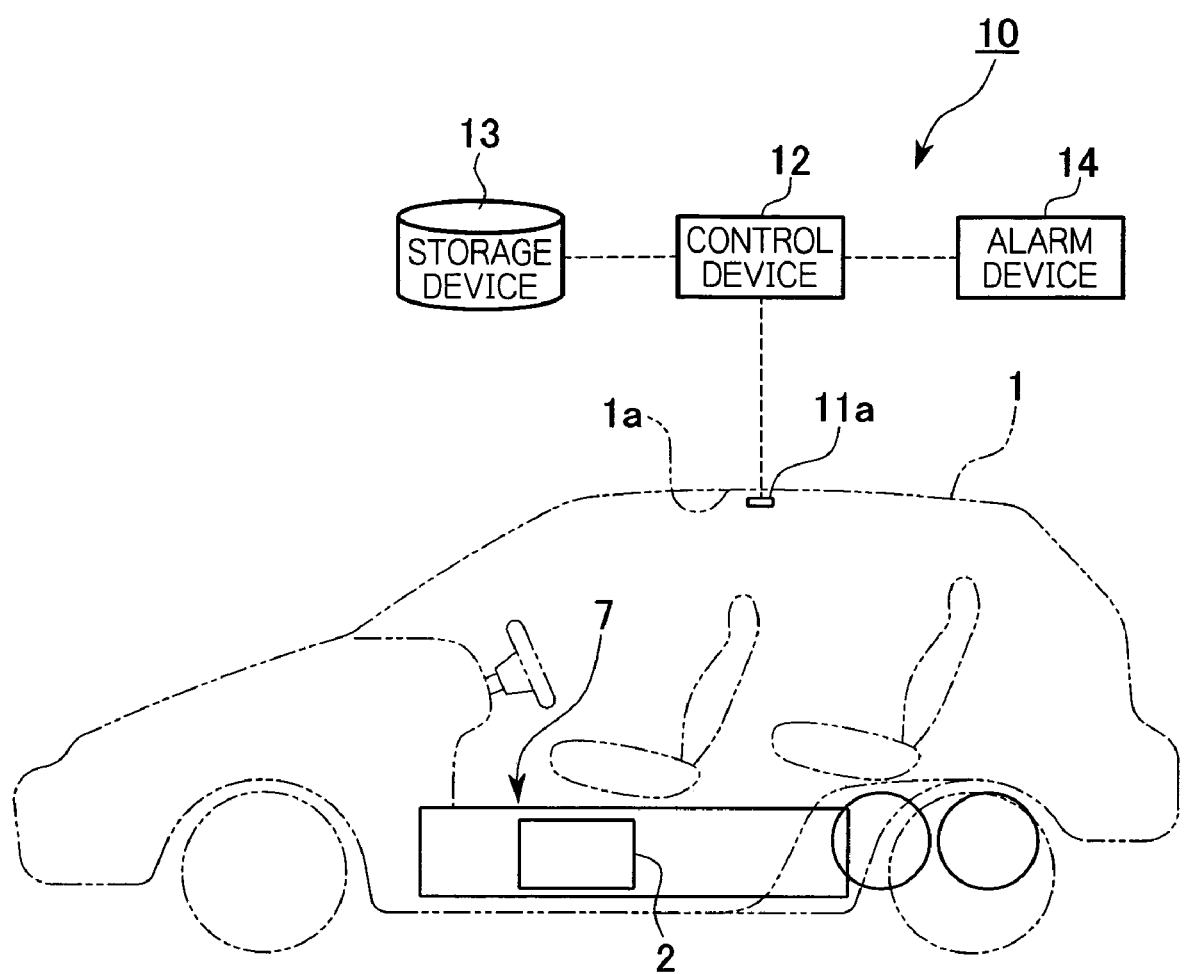
FIG. 1 is a block diagram of the gas sensor degradation diagnosis device according to an embodiment of the present invention.

Below, the gas sensor degradation diagnosis device according to an embodiment of the present invention is explained referring to the drawings.

Figure 2:
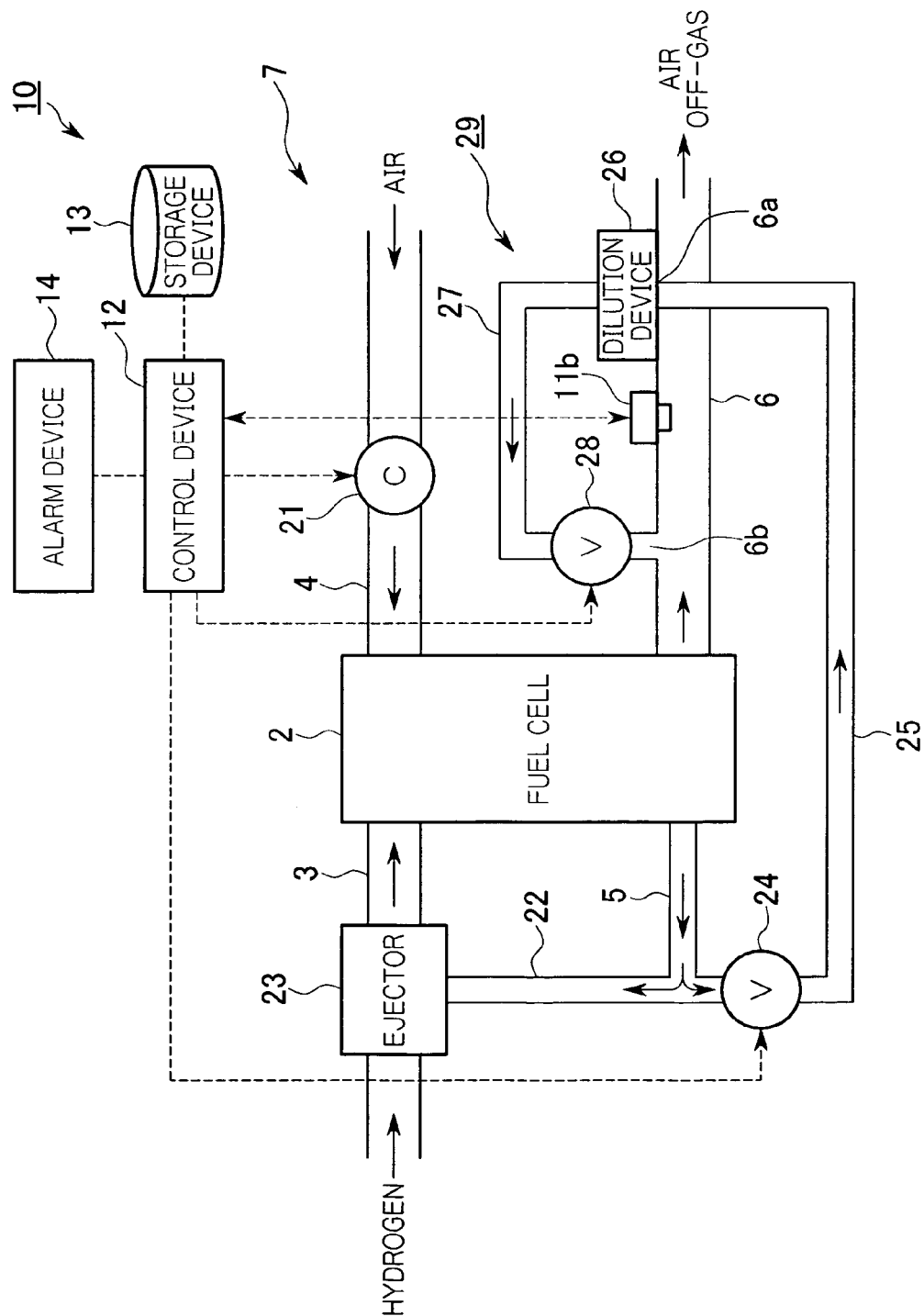
FIG. 2 is a block diagram of the main parts of the fuel cell system having the gas sensor degradation diagnosis device according to an embodiment of the present invention.

The gas sensor degradation diagnosis device according to the present embodiment includes a hydrogen sensor 11a for detecting hydrogen of the prescribed concentration, including zero, in the interior of a vehicle 1 such as a fuel cell vehicle as shown for example in FIG. 1 and devices such as control device 12, storage device 13 and alarm device 14 that diagnose whether or not each gas sensor is degraded with respect to the gas sensor such as hydrogen sensor 11b provided in the outlet side conduit 6 of the oxygen terminal side of the fuel cell system 7 including a fuel cell 2 and conduits 3, 4, 5, and 6 connected to the fuel cell 2, as shown for example in FIG. 2.

The control device 12 is connected to the hydrogen sensor 11a installed in the roof 1a of the vehicle and to hydrogen sensor 11b installed in the outlet side conduit 6 of the oxygen terminal side of the fuel cell 2, determines for example whether or not each hydrogen sensor 11a and 11b is degraded in accordance with the comparison result between the detection signal output from hydrogen sensors 11a and 11b and the prescribed judgment threshold value stored in storage device 13, and outputs an alarm and the like by means of alarm device 14 when degradation is determined. Here, storage device 3 stores maps and the like of the prescribed judgment threshold values for the detection values (outputs) of gas sensors 11a and 11b.

FIG. 2 is a block diagram of the fuel cell system 7, and in this embodiment the fuel cell system 7 is mounted in the vehicle 1 such as a fuel cell vehicle driven by the generated power of the fuel cell 2 as shown for example in FIG. 1.

Fuel cell 2 includes a stack constituted by stacking a number of sets of fuel cells (not shown) each employing a pair of separators to sandwich and hold an electrolyte-electrode structure sandwiching a solid polymer electrolyte membrane consisting of a positive ion exchange membrane or the like with a fuel electrode (anode) and oxygen electrode (cathode).

The gas contact combustion-type hydrogen sensor 11b is provided at the outlet side conduit 6 on the oxygen electrode side. And with respect to the outlet side conduit 6 that is arranged so that, for example, the air off-gas circulates in a horizontal direction, the hydrogen sensor 11b is arranged on the vertically upper portion of this outlet side conduit 6. With this hydrogen sensor 11b, hydrogen of the prescribed concentration, including zero, included in air off-gas that circulates in the outlet side conduit 6 on the oxygen electrode side can be detected.

Furthermore, as shown in FIG. 2, hydrogen discharge path 25 is connected to the outlet side conduit 5 on the fuel electrode side of the fuel cell 2 via purge valve 24, and a dilution device 26 is connected to this hydrogen discharge path 25. The hydrogen off-gas can be discharged through the hydrogen discharge path 25 via the purge valve 24 and, by flowing through the hydrogen discharge path 25, can be introduced to the dilution device 26.

The dilution device 26 is constituted to be able to dilute hydrogen off-gas taken in from the hydrogen discharge path 25 by an appropriate factor using air off-gas taken in from a position 6a further downstream from the hydrogen sensor 11b on the outlet side conduit 6 on the oxygen electrode side and discharge it as dilute gas.

The dilute gas formed in the dilution device 26 is then returned to a position 6b (the dilute gas introduction portion) further upstream from the hydrogen sensor 11b on the outlet side conduit 6 on the oxygen electrode side.

The dilution device 26 is constituted to be able to store an appropriate dilute gas so as to be able to circulate dilute gas in the outlet side conduit 6 even if air off-gas does not flow in the outlet side conduit 6 on the oxygen electrode side when, for example, the fuel cell 2 is stopped.

Here, purge valve 24 and introduction valve 28 are opened and closed by control device 12. When purge valve 24 and introduction valve 28 are opened, hydrogen off-gas flowing through the outlet side conduit 5 on the fuel electrode side is introduced to the dilution device 26 through the hydrogen discharge path 25. Hydrogen off-gas diluted to an appropriate concentration at the dilution device 26 is then discharged as dilute gas to the outlet side conduit 6 on the oxygen electrode side through reflux path 27.

The dilution factor of the dilution device 26 can be preset to a prescribed value. When the hydrogen gas concentration of the hydrogen off-gas is known, the hydrogen gas concentration of the dilute gas is also known. However, because the flow rate of the air off-gas flowing through the outlet side conduit 6 on the oxygen electrode side changes depending on the output of the fuel cell 2, the hydrogen gas concentration in the air off-gas mixed with the dilute gas changes depending on the output of the fuel cell 2.

For this reason, the hydrogen gas concentration of the dilute gas and the dilution factor of the dilution device 26 are set so that, when mixing dilute gas in air off-gas flowing through the outlet side conduit 6 on the oxygen electrode side and performing degradation diagnosis of hydrogen sensor 11b using hydrogen gas contained in the air off-gas after mixing with dilute gas, the hydrogen gas concentration in the air off-gas mixed after mixing with dilute gas is at least a value within the detectable range of the hydrogen sensor 11b.

Furthermore, the distance from the dilute gas introduction portion 6b to the hydrogen sensor 11b is set to the prescribed distance so that dilute gas introduced in the outlet side conduit 6 on the oxygen electrode side reaches the hydrogen sensor 11b in a state of being nearly uniformly mixed with the air off-gas flowing through the outlet side conduit 6 on the oxygen electrode side.

The dilute gas supply device 29 is constituted by the purge valve 24, hydrogen discharge path 25, dilution device 26, reflux path 27 and introduction valve 28.

As shown in FIG. 1, the gas contact combustion-type hydrogen sensor 11a, for example, has a long rectangular case 30 along the horizontal direction of the roof 1a of the vehicle 1 (for example, the lengthwise or sidewise directions of the vehicle 1). As shown in FIG. 2, the gas contact combustion-type hydrogen sensor 11b, for example, has a long rectangular case 30 along the longitudinal direction of the of the outlet side conduit 6 on the oxygen electrode side.

Figure 3:
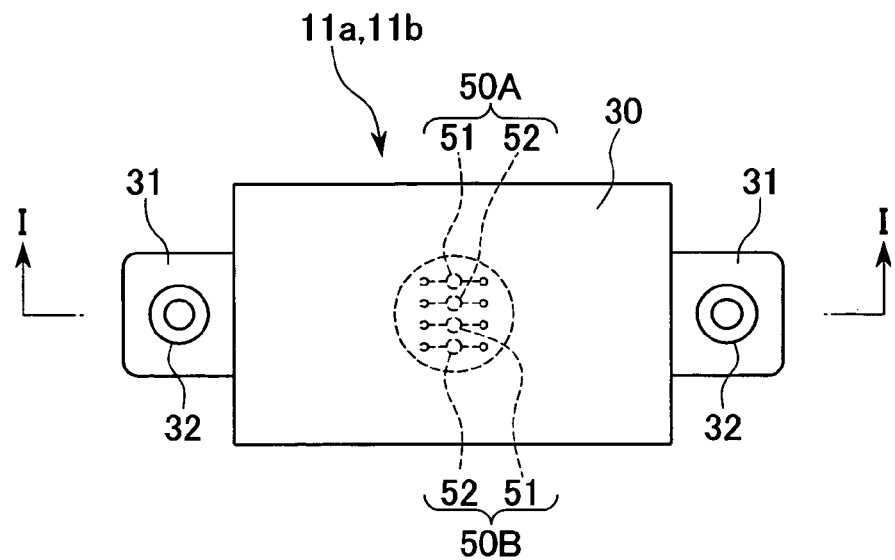
FIG. 3 is a sectional view of the hydrogen sensor shown in FIG. 1 or FIG. 2.

As shown for example in FIG. 3, the case 30 has flanges 31 made of, for example, polyphenylene sulphide on both horizontal end portions. Collars 32 are attached to the flanges 31, and by inserting bolts 33 into these collars 32, the flanges 31 can be tightly fastened to the mounting eyes 6A provided on the outlet side conduit 6 on the oxygen electrode side.

Figure 4:
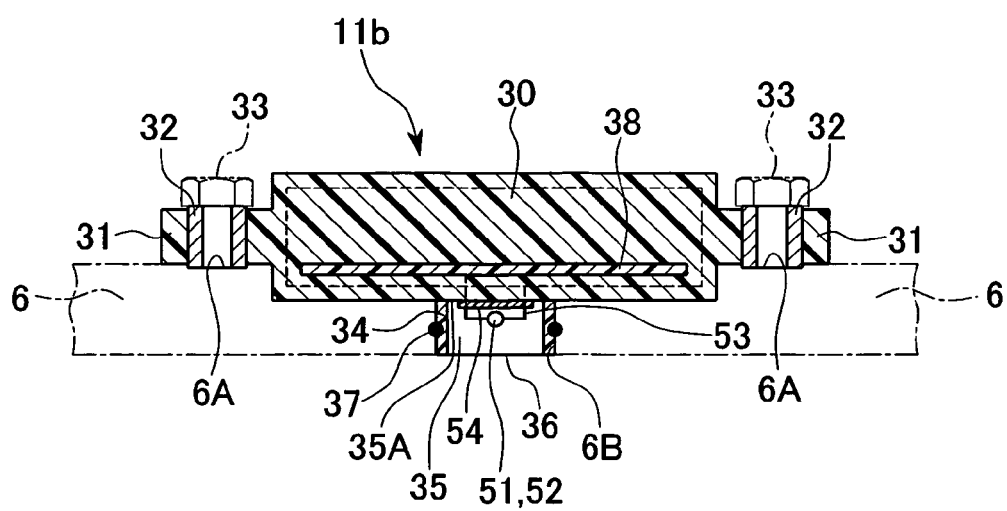
FIG. 4 is a schematic sectional view along line I-I shown in FIG. 3.

Also, as shown in FIG. 4, tube 34 is formed at the end face of case 30 in the thickness direction, with the interior of tube 34 forming a gas detection chamber 35, and the inner circumference of the end of the tube 34 forming the opening that is gas introduction portion 36. As shown in FIG. 4, for example, in hydrogen sensor 11b set in the outlet side conduit 6 on the oxygen electrode side, tube 34 passes from the outer side to the through-hole B6 of the outlet side conduit 6 on the oxygen electrode side. Then, sealant 37 is attached to the outer circumference of tube 34 at the gas sensor 11b attached to the outlet side conduit 6 on the oxygen electrode side. This sealant 37 ensures air tightness with the inner wall of through-hole 6B of the outlet side conduit 6 on the oxygen electrode side.

The hydrogen sensor 11a provided on the roof 1a is set so that the end surface of tube 34 is nearly flush with the roof 1a. And the hydrogen sensor 11b provided at the outlet side conduit 6 on the oxygen electrode side is set so that the end surface of tube 34 is nearly flush with the inner surface of the outlet side conduit 6 on the oxygen electrode side. For example, the ambient gas in the car interior that is the gas subject to inspection by the hydrogen sensors 11ab is introduced to the gas detection chamber 35 vertically with respect to the roof 1a. In addition, air off-gas that is the gas subject to inspection by hydrogen gas sensor 11b is introduced to the gas inspection chamber 35 vertically with respect to the outlet side conduit 6 on the oxygen electrode side.

A circuit substrate 38 sealed by resin is provided in the case 30, and a plurality of sets of detector elements arranged in mutually close contact in the interior of tube 34, such as two sets of reference detector member 50A and common detector member 50B, are connected to the circuit substrate 38.

Detector members 50A and 50B are respectively constituted to be counterparts to detector elements 51 and temperature compensating elements 52. Elements 51 and 52 are arranged so as to form a pair with a prescribed clearance at a position separated by the prescribed distance in the thickness direction of hydrogen sensors 11a and 11b from the base 54 disposed on the bottom face 35A of the gas detection chamber 35 by a plurality of, such as eight, pins 53 connected to the circuit substrate 38.

That is, the two pairs of detector members 50A and 50B are disposed alongside each other at a position of the same height from the base 54 in the gas detection chamber 35.

The arrangement direction of each element 51 and 52 (for example, the extending direction of the straight line connecting the center positions of elements 51 and 52) may be set to an arbitrary direction. For example, the arrangement direction of elements 51 and 52 in the hydrogen sensor 11b attached to the outlet side conduit 6 on the oxygen electrode side may be set independently of the flow direction of the air off-gas flowing through the outlet side conduit 6.

In the case of the plurality of sets of detector members being arranged in close proximity, the deviation between each concentration detection value is within the prescribed deviation in the case of deviations between each detection value (concentration detection value) of the actual concentration of the gas under detection detected by the plurality of sets of detector members changing only in response to the relative arrangement position between the detector members. For example, the two sets of reference detector member 50A and common detector member 50B are arranged so that the deviation between each concentration detection value of the hydrogen gas concentration detected by detector members 50A and 50B is within the prescribed ratio with respect to the concentration values.

Here, the required deviation is taken to be, for example, within ±20% with respect to each concentration detection value, and more preferably, for example, within ±10%, and still more preferably, within ±5%.

The deviation of each detector member detection value is set to correspond to the actual concentration detection values of the detected gas under detection, and is not, for example, simply the deviation calculated with respect to the output value output from each detector member. For example, even when the suitable offset value is set with respect to the output value in each detector member, it is calculated to correspond to each concentration detection value obtained after correcting these offset values.

Figure 5:
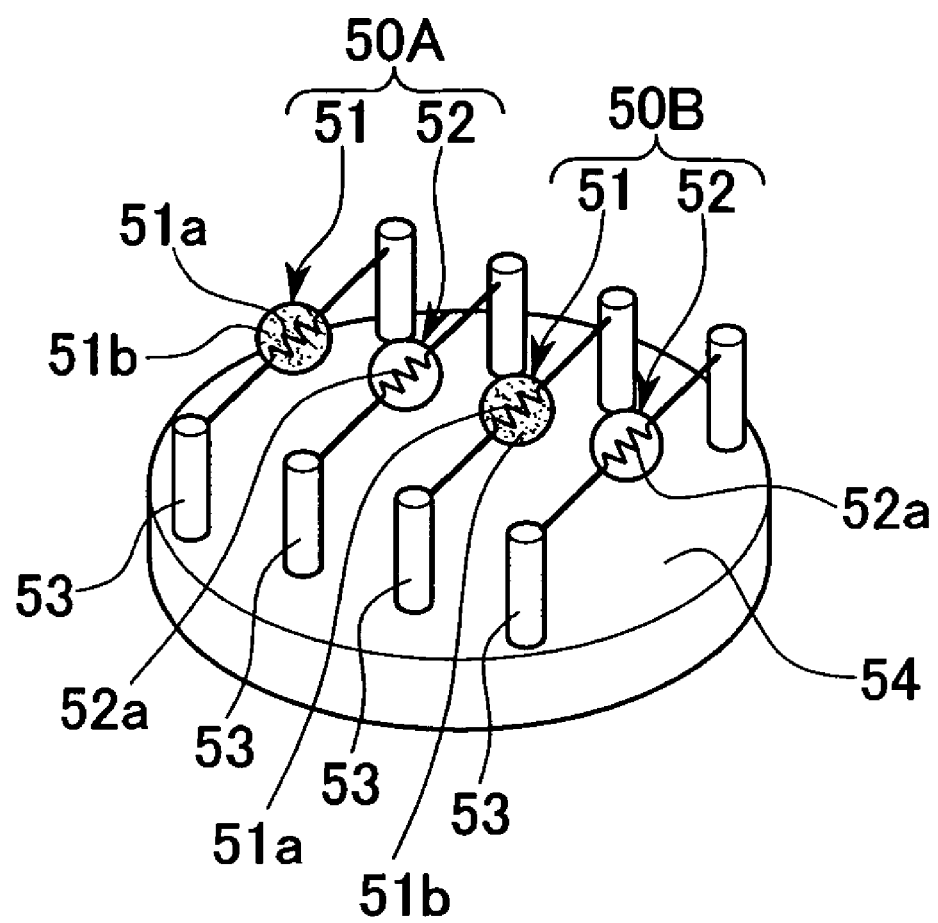
FIG. 5 is a perspective view of the main parts of the hydrogen sensor shown in FIG. 1 or FIG. 2.

The detector elements 51 are well-known elements. As shown for example in FIG. 5 and FIG. 6, the surface of metal coil 51a including platinum and the like having a high temperature coefficient with respect to the electrical resistance is formed to be covered with a carrier such as alumina supporting a catalyst 51b including noble metals and the like that are active with respect to hydrogen that is the gas under detection.

Temperature compensating elements 52 are inert with respect to the gas under detection, and the surface of coil 52a equivalent to detector element 51 for example is covered with a carrier such as alumina.

Detection of the hydrogen gas density has come to be possible by using the difference in electrical resistance values that occur between the detector element 51, which becomes a high temperature due to the heating of the combustion reaction generated when hydrogen that is the gas under detection contacts the catalyst 51b of the detector element 51, and the temperature compensating element 52, which is a lower temperature than the detector element 51 without the combustion reaction by the gas under detection, and compensating the changed portion of the electrical resistance values with the atmospheric temperature.

Figure 6:
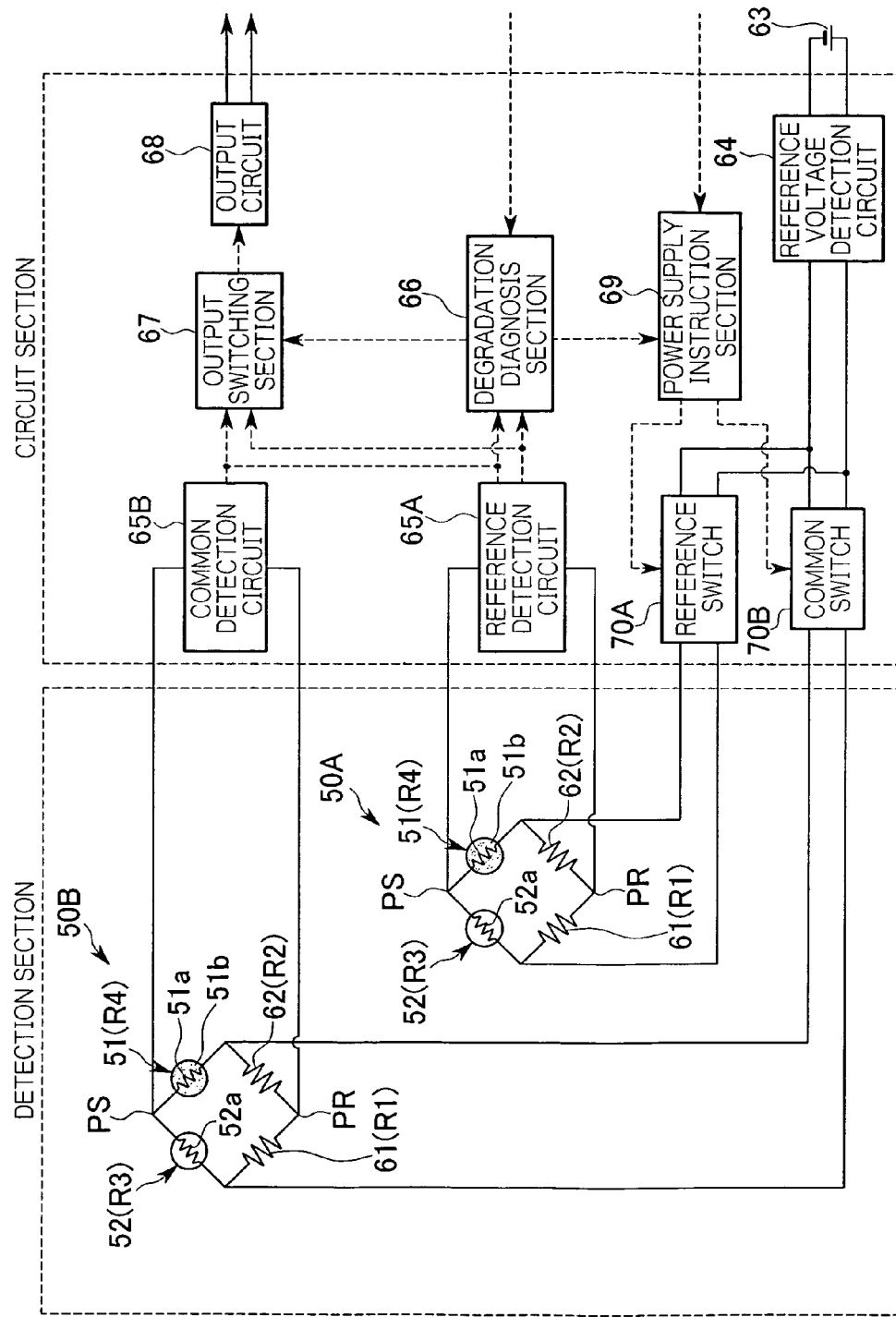
FIG. 6 is a block diagram of the detection section and circuit section constituting the hydrogen sensor shown in FIG. 1 or FIG. 2.

As shown for example in FIG. 6, with respect to each of the detector members 50A and 50B, the branch in which detector element 51 (resistance value R4) and temperature compensating element 52 (resistance value R3) are connected in series, and the branch in which fixed resistance 61 (resistance value R1) and fixed resistance 62 (resistance value R2) are connected in series are connected in parallel with respect to the reference voltage generating circuit 64 that applies a prescribed reference voltage based on the voltage supplied from the external power source 63 to form bridge circuits. Then in each bridge circuit, between a contact point PS, which is common to detector element 51 and temperature compensating element 52, and a contact point PR, which is common to fixed resistances 61 and 62, reference detection circuit 65A and common detection circuit 65B, which detect the voltage between these connection points PS and PR, are connected.

Here, when hydrogen that is the gas under detection does not exist in the gas subject to inspection introduced in the gas detection chamber 35, the bridge circuit is balanced so that it is in a state of $R1 \times R4 = R2 \times R3$, and the outputs of detection circuits 65A and 65B become zero. On the other hand, when hydrogen exists, hydrogen combusts in the catalyst 51b of detector element 51, causing the temperature of coil 51a to rise, and resistance value R4 increases. In contrast, in the temperature compensating elements 52, hydrogen does not combust, and so the resistance value R3 does not change. Because of this, the balance of the bridge circuit is broken, causing a voltage changing with an increasing tendency in response to increasing changes of the hydrogen concentration to be impressed on each of the detection circuits 65A and 65B.

The voltage detection values output from each of the detection circuits 65A and 65B are output to degradation diagnosis section 66 or output switching section 67.

Here, the degradation diagnosis section 66, as described below, performs degradation diagnosis of each detector member 50A and 50B by relative diagnosis, which relatively compares the detection values of reference detector member 50A and common detector member 50B, or absolute diagnosis, which mutually and independently compares the detection value of reference detector member 50A and detection value of common detector member 50B with the prescribed reference value, and outputs the result of diagnosis, for example, to the output switching section 67, power supply instruction section 69 and alarm section 14.

The output switching section 67 outputs the detection result output from either one of the reference detection circuit 65A or common detection circuit 65B, for example, to the output circuit 68 depending on the detection result input from the degradation diagnosis section 66. For example, the output switching section 67, during operation of the vehicle 1, performs switching so that the detection result output from, for example, the reference detector member 50A is output to the output circuit 68 when the diagnosis result showing degradation of the common detector member 50B is input from the degradation diagnosis section 66 by the condition of outputting the detection result output from the common detection circuit 65B to the output circuit 68.

Then, output circuit 68 outputs the input detection value to the control device 12, where the hydrogen concentration is calculated based on the hydrogen concentration map and the like preset in accordance with the change in the voltage detection value.

Between each detector member 50A and 50B and the reference voltage generating circuit 64, switchable reference switch 70A and common switch 70B are provided in accordance with the control instruction input from the power supply instruction section that turns on/off current from the reference voltage detection circuit 64 to each detector member 50A and 50B.

Here, the power supply instruction section 69 controls the switching operation of each switch 70A, 70B based on, for example, the diagnosis result of the degradation diagnosis input from the degradation diagnosis section 66, for example the control instruction input from the control device 12, and for example the prescribed timing.

For example, during operation of the fuel cell 2, normally current is always supplied to the bridge circuit in which common detector member 50B is incorporated in each hydrogen sensor 11a and 11b by the power supply instruction section 69. The hydrogen gas concentration in the air off-gas flowing in the interior of the vehicle 1 and the outlet side conduit 6 on the oxygen electrode side is detected by this common detector element 50B. Then current is normally cut to the bridge circuit in which the reference detector member 50A is incorporated by the power supply instruction section 69 so that detection of hydrogen gas concentration by the reference detector element 50 is not performed.

In this case, degradation of the catalyst attached to the detector elements 51 by silicon poisoning, sulfur poisoning or water absorption is known to proceed only when the detector elements 51 are being powered. Accordingly, there is normally a risk of the catalyst attached to detector element 51 of common detector member 50B being degraded by silicon, sulfur and water contained in the air off-gas through use over time. On the other hand, since power is normally cut to the reference detector member 50A, degradation of the catalyst attached to the detector element 51 of the reference detector member 50A due to silicon, sulfur and water contained in the air off-gas is inhibited.

When degradation diagnosis of each hydrogen sensor 11a and 11b is performed in a prescribed period, the power supply instruction section 69 supplies current to each bridge circuit in which the reference detector member 50A or common detector member 50B is incorporated to execute detection of the hydrogen gas concentration of the gas subject to inspection respectively by both reference detector member 50A or common detector member 50B.

Here, the prescribed period is, in addition to, for example, the timing each time the operation duration of the fuel cell 2 progresses for the prescribed time, also for example when the ignition switch that instructs the starting of the vehicle is on in preparation for starting the vehicle, for example when the ignition switch is off in preparation for the next starting of the vehicle, and corresponding to the risk of degradation of each hydrogen sensor 11a and 11b, for example, when each hydrogen sensor 11a and 11b is exposed to the gas under detection having a hydrogen gas concentration exceeding the prescribed concentration for more than the specified period and when for example each hydrogen sensor 11a and 11b is exposed to the gas to be detected having a humidity exceeding the prescribed humidity for over the prescribed time.

Furthermore, the prescribed period is for example during starting of the fuel cell 2, regular operation and idling operation and the like of the vehicle 1, when degradation diagnosis can be executed by the gas under detection of a stable concentration by each gas density of the hydrogen off-gas and air off-gas discharged from the fuel cell 2 being relatively stable, when the degradation diagnosis can be executed for a plurality of different concentrations of gas under detection by the time change of each gas concentration of the hydrogen off-gas and air off-gas discharged from the fuel cell 2 is relatively large when for example during excessive operation of the fuel cell 2, and when self diagnosis processing of for example the breaking detection is executed for each prescribed duration with respect to each hydrogen sensor 11a and 11b.

In degradation diagnosis corresponding to the on/off of the ignition switch and degradation diagnosis corresponding to the operating condition of the fuel cell 2, the degradation diagnosis process commences with a control instruction input from the control device 12. In degradation diagnosis at each prescribed time and degradation diagnosis corresponding to the operating condition of each hydrogen sensor 11a and 11b, the degradation diagnosis process is started by, for example, the degradation diagnosis section 66 and the like without requiring a control instruction input from the control device 12.

In relative diagnosis executed by the aforementioned degradation diagnosis section 66, diagnosis of whether the common detector member 50B is degraded or not is performed by comparing the output value base on the reference detector member 50A (hereafter, the output value of reference detector member 50A) and the output value based on the common detector member 50B (hereafter, the output value of the common detector member 50B).

In other words, degradation is inhibited because the catalyst attached to the detector element 51 of the reference detector member 50A is not electrically connected during normal operation. Because of this, reference detector member 50A can output a more accurate output value corresponding to the hydrogen gas concentration. When the output value of the common detector member 50B, upon comparison with the output value of the reference detector member 50A, is in the prescribed allowable range, the common detector member 50B can be judged as normal.

Accordingly, in this relative diagnosis, gas subject to inspection having equivalent hydrogen gas concentration may be supplied to the reference detector member 50A and the common detector member 50B.

In this relative diagnosis, depending to the diagnosis results, degradation diagnosis may be executed without altering the ambient gas condition of each hydrogen sensor 11a and 11b around the time of diagnosis simply by electrically connecting each bridge incorporating the reference detector member 50A and the common detector member 50B by means of the power supply instruction section 69. Furthermore, degradation diagnosis may also be executed by performing settings so that the hydrogen gas concentration of the gas subject to inspection with respect to each hydrogen sensor 11a and 11b is at least a value within the detectable range of each hydrogen sensor 11a and 11b.

For example, by opening the purge valve 24 and the introduction valve 28 with the control device 12 with respect to the hydrogen sensor 11b disposed on the outlet side conduit 6 of the oxygen terminal side, dilute gas is supplied to the outlet side conduit 6 of the oxygen terminal side, and the hydrogen gas concentration of the air off-gas serving as the gas subject to inspection is set to an appropriate value within the detectable range of the hydrogen sensor 11b.

In addition, the presence of a zero-point fluctuation with respect to the output value of the common detector member 50B can be detected when supplying gas whose hydrogen gas concentration is zero or a value less than the detectable range of each hydrogen sensor 11a and 11b, such as air, as the gas subject to inspection. Furthermore, by acquiring beforehand the interrelation of the fluctuation level of this zero-point fluctuation and the degradation state of each hydrogen sensor 11a and 11b, the degradation state on the high concentration side can be estimated.

In absolute diagnosis executed by the degradation diagnosis section 66, the control device 12 supplies gas subject to inspection with a known concentration, that is, gas subject to inspection with a prescribed hydrogen gas concentration including zero (gas for absolute inspection), to the reference detector member 50A and the common detector member 50B. Then degradation diagnosis section 66 mutually and independently compares the detection value of reference detector member 50A and detection value of common detector member 50B with the prescribed value corresponding to the gas for absolute inspection of a known concentration. When the output values of each detector member 50A and 50B are within the prescribed allowable range with respect to the prescribed value, each corresponding detector member 50A and 50B is judged to be normal, and when outside the prescribed allowable range, each corresponding detector member 50A and 50B is judged to be abnormal.

In this absolute diagnosis, depending on the diagnosis results, degradation diagnosis may be executed with respect to each detector member 50A and 50B or both detector members 50A and 50B by electrically connecting the bridge circuit of either one of the reference detector member 50A and the common detector member 50B, or electrically connecting each bridge circuit of both the reference detector member 50A and the common detector member 50B by means of the power supply instruction section 69.

Also, when supplying gas for absolute inspection of a known concentration, for example, by opening the purge valve 24 and the introduction valve 28 with the control device 12 with respect to the hydrogen sensor 11b disposed on the outlet side conduit 6 of the oxygen terminal side, dilute gas is supplied to the outlet side conduit 6 of the oxygen terminal side, and the hydrogen gas concentration of the air off-gas serving as the gas subject to inspection is set to an appropriate value within the detectable range of the hydrogen sensor 11b.

In addition, the presence of a zero-point fluctuation with respect to each output value of the reference detector member 50A and common detector member 50B can be detected when supplying gas whose hydrogen gas concentration is zero or a value less than the detectable range of each hydrogen sensor 11a and 11b, such as air, as the gas subject to inspection.

Then the diagnosis result of the degradation diagnosis section 66 is output to the control device 12. When it is diagnosed that for example that an abnormality has occurred in the reference detector member 50A or common detector member 50B, the control device 12 notifies the driver or the like with the alarm device 14 that each hydrogen sensor 11a and 11b has degraded.

The gas sensor degradation diagnosis device 10 according to the present embodiment is provided with the aforementioned constitution, and next the operation of the gas sensor degradation diagnosis device 10 is explained referring to the drawings.

Below, the process of diagnosing degradation of, for example, the hydrogen sensor 11a attached to the roof 1a of the vehicle 1 and the hydrogen sensor 11b attached to the outlet side conduit 6 of the oxygen terminal side of the fuel cell 2 by relative diagnosis is explained.

Described here is, for example in a normal operating condition of the vehicle 1 in which generation of electrical energy is being performed in the fuel cell 2, the condition in which, with respect to each hydrogen sensor 11a and 11b, power is always supplied to the bridge circuit incorporating common detector member 50B, power is cut off to the bridge circuit incorporating the reference detector member 50A, the hydrogen gas concentration of the ambient gas in the vehicle interior is detected by the common detector member 50B of the hydrogen sensor 11a, and the hydrogen gas concentration of the air off-gas discharged from the outlet side conduit 6 of the oxygen terminal side of the fuel cell 2 is detected by the common detector member 50B of the hydrogen sensor 11b.

Figure 7:
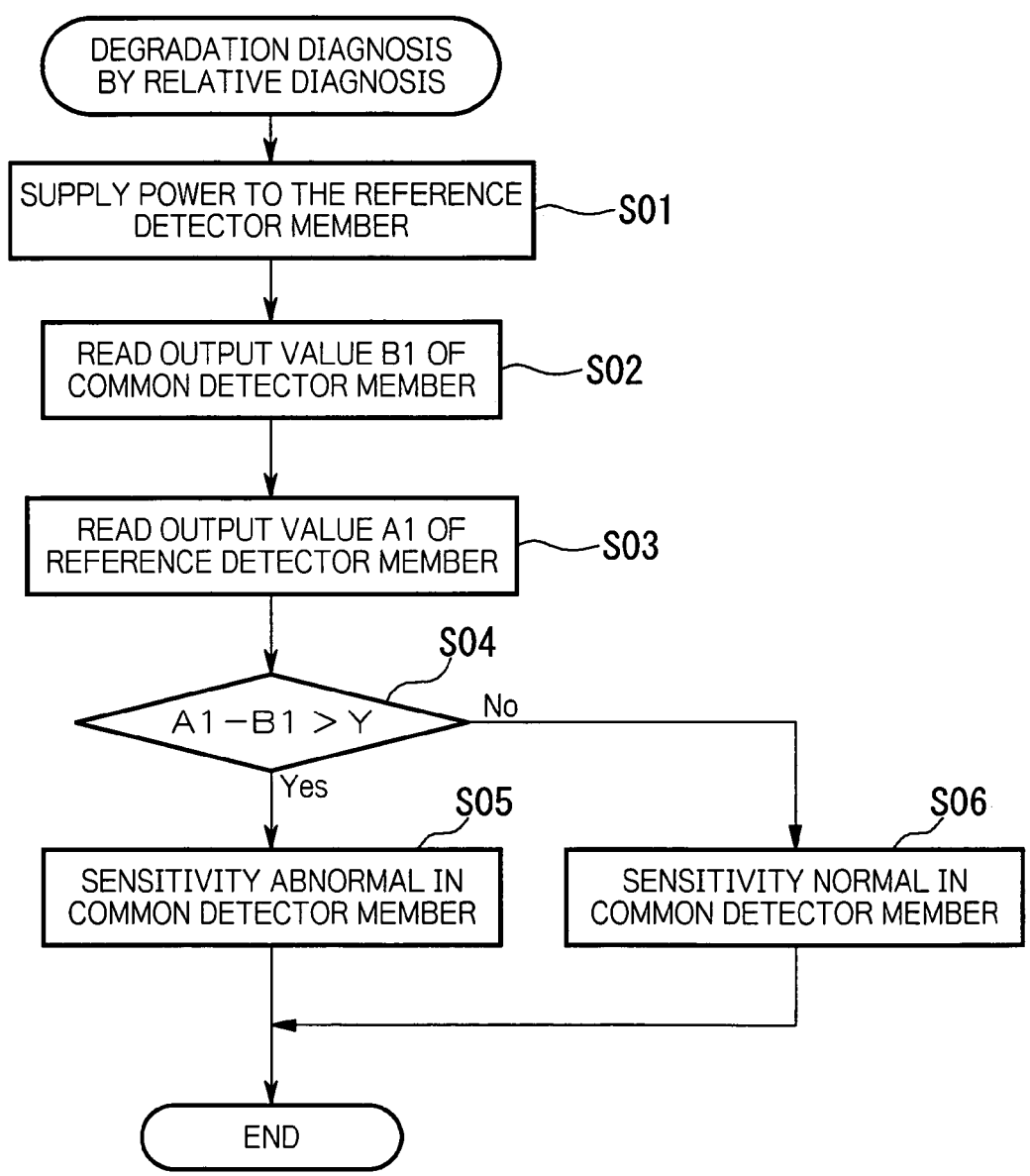
FIG. 7 is a flowchart showing the process of degradation diagnosis by a gas sensor degradation diagnosis method according to an embodiment of the present invention, particularly relative diagnosis.

First, in for example step S01 shown in FIG. 7, power is supplied to the reference detector member 50A of each hydrogen sensor 11a and 11b.

Then, in step S02, the output value B1 of common detector member 50B is read for each hydrogen sensor 11a and 11b, and then in step S03, the output value A1 of reference detector member 50A is read for each hydrogen sensor 11a and 11b.

In step S04, the difference (comparison value) between the output value B1 of common detector member 50B and output value A1 of the reference detector member 50A for each hydrogen sensor 11a and 11b is found, and a determination is made as to whether this difference (A1−B1) exceeds the prescribed value Y When the judgment result is "YES", that is, when it exceeds the prescribed value Y, step S05 is proceeded to, where it is judged that the detector element 51 of the common detector member 50B has a response anomaly, i.e., its output value has decreased due to degradation of the catalyst of the detector element 51, each hydrogen sensor 11a and 11b is determined to be degraded and the series of processes ends.

On the other hand, when the judgment result is "NO", that is when less than or equal to the prescribed value Y, step S06 is proceeded to, where it is judged that detector element 51 of the common detector member 50B has a normal response and each hydrogen sensor 11a and 11b is not degraded, and the series of processes ends.

The prescribed value Y is taken to be a value such as 20% of for example each output value A1 or output value B1 (for example, 0.2−A1 or 0.2−B1).

Below, the process of diagnosing degradation of each hydrogen sensor 11a and 11b, particularly of the hydrogen sensor 11*b* attached to the outlet side conduit 6 of the oxygen terminal side of the fuel cell 2, is explained.

Described here is, for example in a normal operating condition of the vehicle 1 in which generation of electrical energy is being performed in the fuel cell 2, the condition in which, with respect to hydrogen sensor 11*b*, power is always supplied to the bridge circuit incorporating common detector member 50B, power is cut off to the bridge circuit incorporating the reference detector member 50A, and the hydrogen gas concentration of the air off-gas discharged from the outlet side conduit 6 of the oxygen terminal side of the fuel cell 2 is detected by common detector member 50B.

Figure 8:
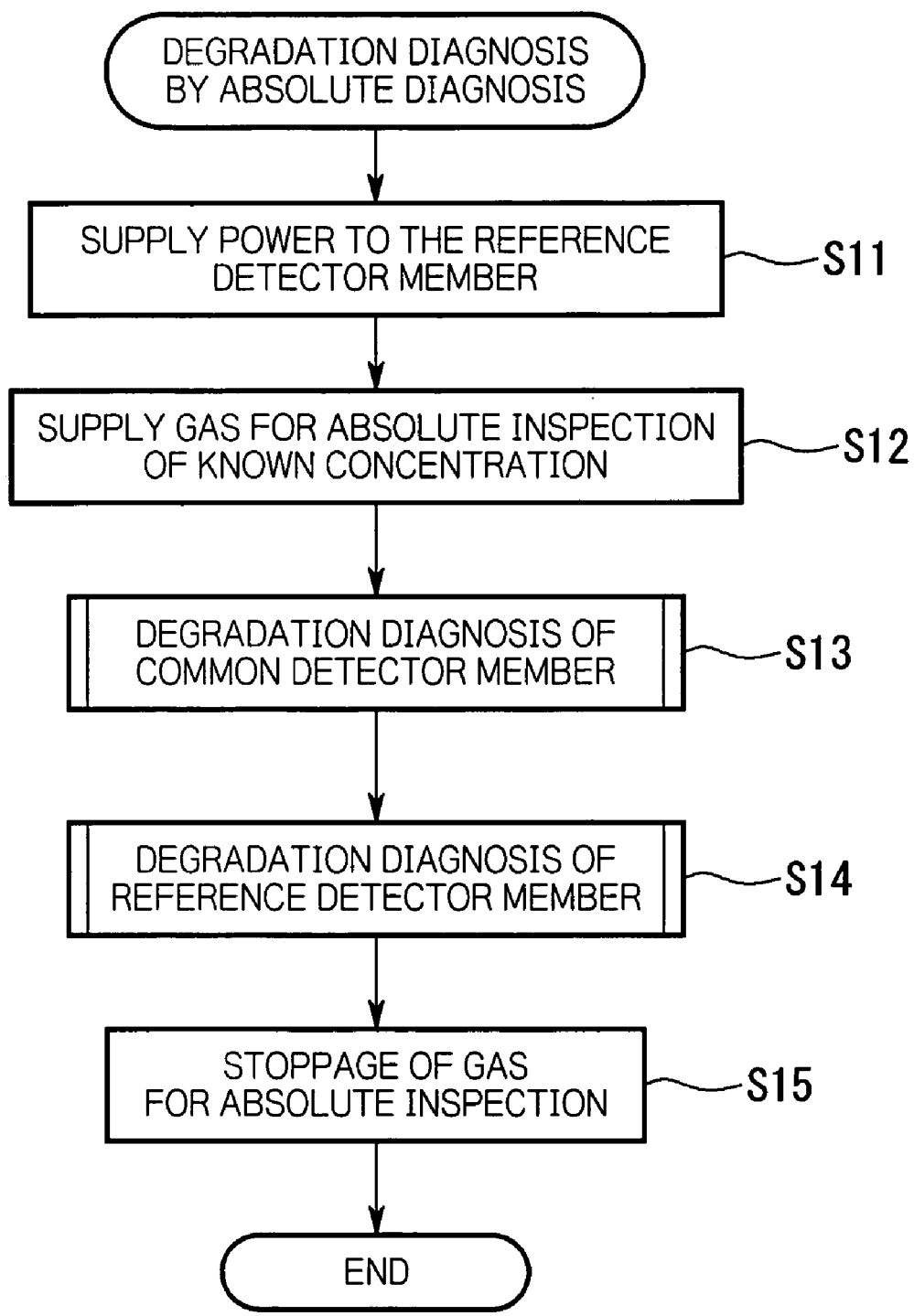
FIG. 8 is a flowchart showing the process of degradation diagnosis by a gas sensor degradation diagnosis method according to an embodiment of the present invention, particularly absolute diagnosis.

First, in for example step S11 shown in FIG. 8, power is supplied to the reference detector member 50A of hydrogen sensor 11*b*.

Then, in step S12 the gas subject to inspection having a hydrogen gas concentration of a known concentration (gas for absolute inspection) is supplied to the outlet side conduit 6 of the oxygen terminal side.

Here, by opening for example the purge valve 24 and the introduction valve 28 with the control device 12, the dilute gas in which the hydrogen off-gas is diluted by the air off-gas at a prescribed dilution factor is supplied to the outlet side conduit 6 of the oxygen terminal side, and the hydrogen gas concentration of the air off-gas after mixing of the dilute gas is set so as to be the prescribed known concentration.

Next, in step S13, a degradation diagnosis process (FIG. 9) is executed for the common detector member 50B to be described, and in step S14, a degradation diagnosis process (FIG. 10) is executed for reference detector member 50A to be described.

In step S15, the purge valve 24 and the introduction valve 28 are closed by the control device 12, the supply of gas for absolute inspection having a hydrogen gas concentration that is a known concentration is stopped, and the series of processes ends.

Below, the degradation diagnosis process is explained for the common detector member 50B in the aforementioned S13.

Figure 9:
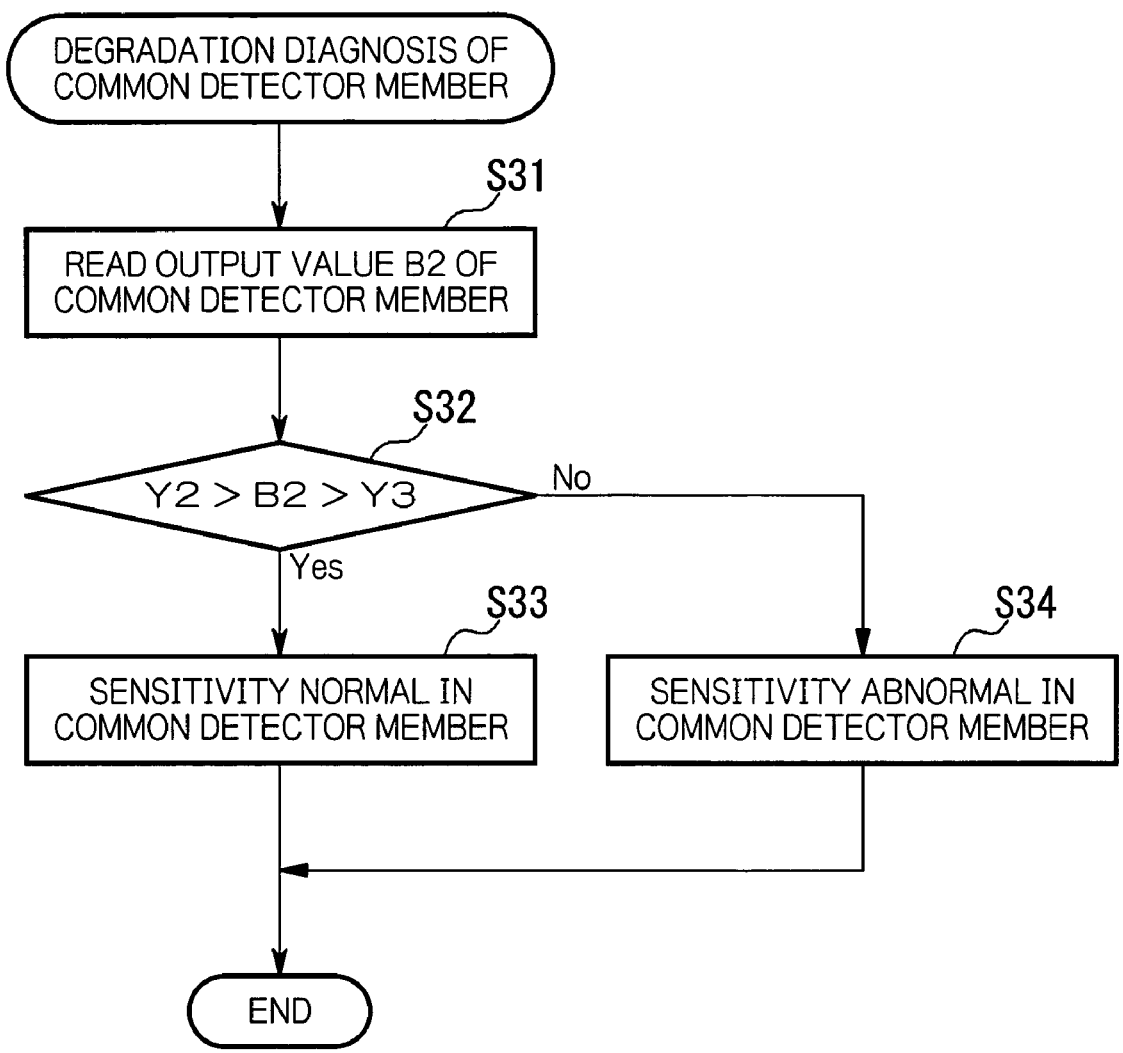
FIG. 9 is a flowchart showing the process of degradation diagnosis of common detector members shown in FIG. 8.

First, in S31 shown in FIG. 9, the output value B2 of the common detector member 50B is read, and the next step S32 is proceeded to, where it is determined whether or not output value B2 of the common detector member 50B is within the range of prescribed value Y2 to prescribed value Y3.

When the determination result is "YES" (Y2>B2>Y3), step S33 is proceeded to, where it is determined that the detector element 51 of the common detector member 50B has a normal response, and then the series of processes ends.

On the other hand, when the determination result is "NO" (B2$\leq$Y3, or B2$\geq$Y2), step S34 is proceeded to, where it is determined that the detector element 51 of common detector member 50B has a response anomaly, and then the series of processes ends.

Below, the degradation diagnosis process is explained for the reference detector member 50A in the aforementioned S14.

Figure 10:
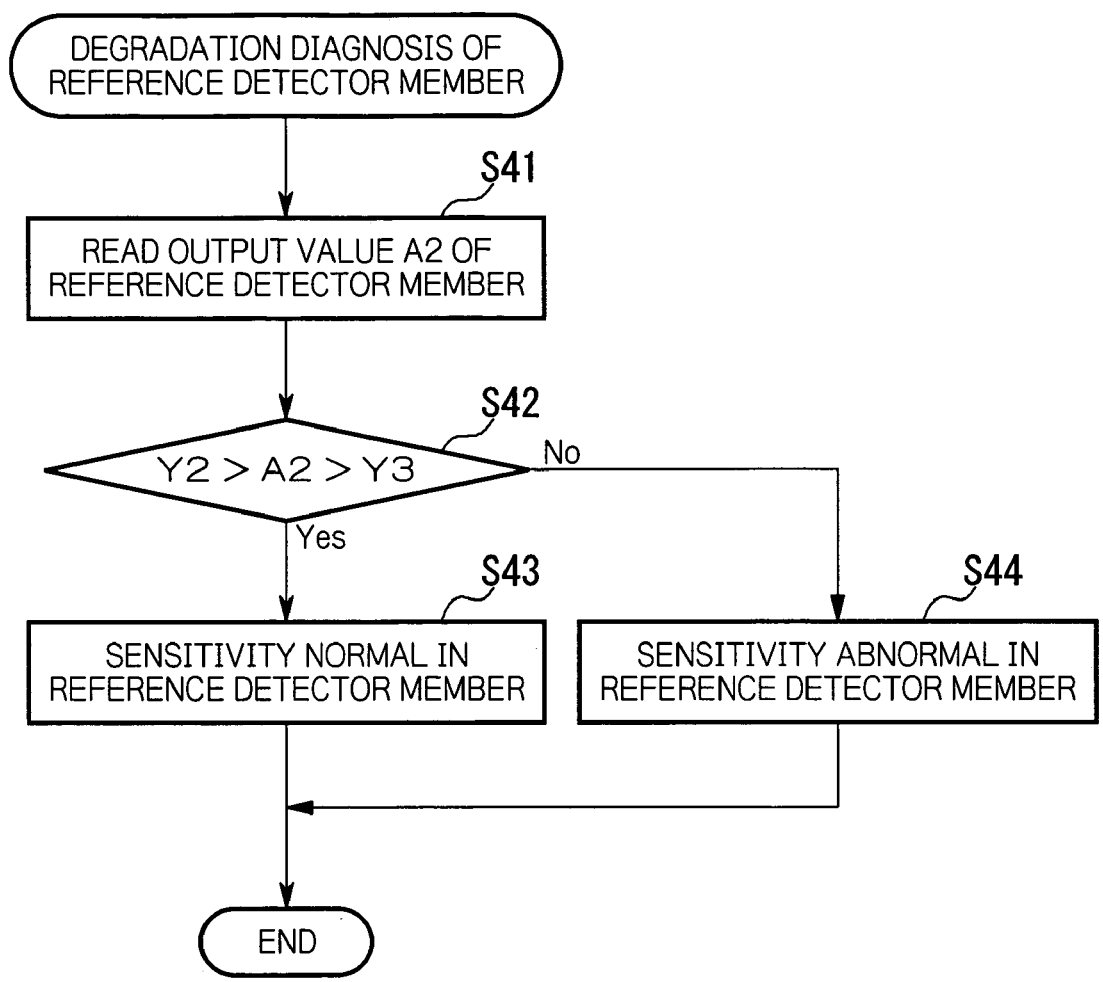
FIG. 10 is a flowchart showing the process of degradation diagnosis of reference detector members shown in FIG. 8.

First, in S41 shown in FIG. 10, the output value A2 of the reference detector member 50A is read, and the next step S42 is proceeded to, where it is determined whether or not output value A2 of the reference detector member 50A is within the range of prescribed value Y2 to prescribed value Y3.

When the determination result is "YES" (Y2>A2>Y3), step S43 is proceeded to, where it is determined that the detector element 51 of the reference detector member 50B has a normal response, and then the series of processes ends.

On the other hand, when the determination result is "NO" (A2$\leq$Y3, or A2$\geq$Y2), step S44 is proceeded to, where it is determined that the detector element 51 of common detector member 50B has a response anomaly, and then the series of processes ends.

The degradation diagnosis process by absolute diagnosis in the aforementioned steps S11 to step S15 is carried out at a lower frequency than the execution frequency of degradation diagnosis by relative diagnosis in, for example, the aforementioned step S01 to step S06, being executed once for every prescribed multiple executions of the degradation diagnosis by relative diagnosis, or when the fuel cell 2 is stopped.

As stated above, according to the gas sensor degradation diagnosis device 10 according to the present embodiment, in a normal operating condition of the vehicle 1, by power always being connected to the bridge circuit incorporating common detector member 50B and being cut off to the bridge circuit incorporating the reference detector member 50A, degradation of the reference detector member 50A can be inhibited compared to the common detector member 50B. During degradation diagnosis of the common detector member 50B, power is supplied to both the common detector member 50B and reference detector member 50A, and by relatively comparing the output value of common detector member 50B and the output value of reference detector member 50A, it can be easily diagnosed whether common detector member 50B is degraded or not.

Also, degradation diagnosis of the reference detector member 50A serving as a reference when relatively diagnosing the degradation diagnosis of the common detector member 50B can be, so to speak, absolutely diagnosed by the output value of the reference detector member 50A. Doing so can enhance the diagnostic accuracy of the degradation diagnosis of common detector member 50B by relative diagnosis.

In addition, according to the gas sensor degradation diagnosis method according to the present embodiment, detection of the hydrogen gas concentration is first executed by both the reference detector member 50A and common detector member 50B simultaneously with regard to the gas subject to inspection of each hydrogen sensor 11*a* and 11*b* by the degradation diagnosis process according to relative diagnosis. By relatively comparing the output value of the reference detector member 50A and the output value of the common detector member 50B at this time, it can be easily diagnosed whether common detector member 50B is degraded or not. Accordingly, degradation diagnosis is possible even if the hydrogen gas concentration of the gas subject to inspection during degradation diagnosis is not constant but fluctuating. Furthermore, it is not necessary for the hydrogen gas concentration of the gas subject to inspection to be known, with diagnosis possible just by supplying gas subject to inspection with an arbitrary hydrogen gas concentration. Because of this, during operation of the fuel cell 2 and the like, degradation diagnosis of each hydrogen sensor 11*a* and 11*b* can be easily performed just by connecting power to each bridge circuit incorporating the reference detector member 50A and the common detector member 50B.

According to degradation diagnosis by absolute diagnosis using gas subject to inspection having a hydrogen gas concentration of a known concentration (gas for absolute inspection), the reference detector member 50A and common detector member 50B can be independently diagnosed. By doing so, as the number of executions of degradation diagnosis processing by, for example, relative diagnosis increases, the frequency of electrical connection to the reference detector member 50A, which is normally electrically disconnected, increases, abnormal conditions can be definitely detected even when the catalyst of the detector element 51 in the reference detector member 50A is slowly degrading or an unanticipated anomaly occurs in the reference detector member 50A.

Since degradation diagnosis of the common detector member 50B is independently performed in addition to the reference detector member 50A, the reliability of the diagnosis result of the common detector member 50B in the degradation diagnosis process by relative diagnosis is enhanced.

Also, using the dilute gas being hydrogen off-gas diluted by air off-gas at a prescribed dilution factor in advance as the gas subject to inspection having a hydrogen gas concentration of a known concentration (gas for absolute inspection) enables degradation diagnosis of the reference detector member 50A to be easily performed without removing the hydrogen sensor 11b from the fuel cell system.

Other Embodiments

Figure 11:
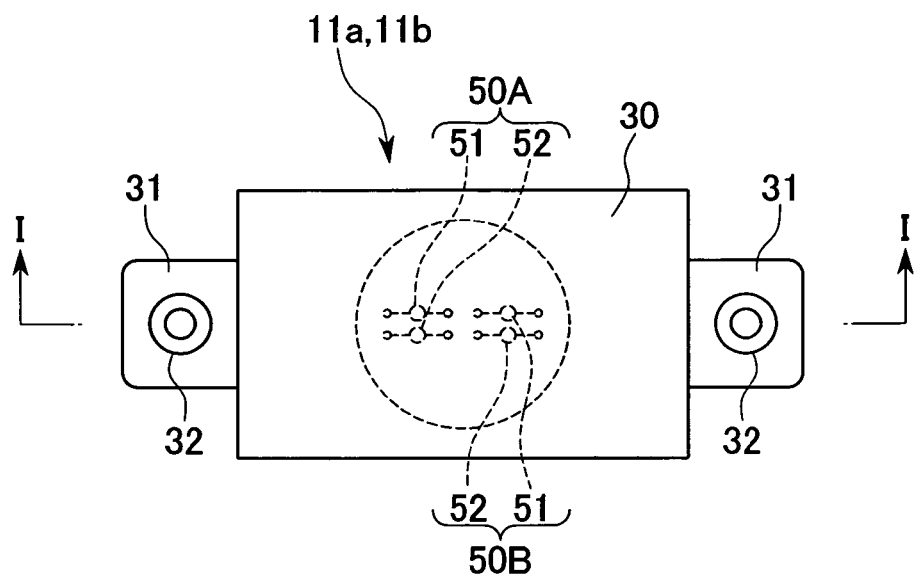
FIG. 11 is a sectional view of the hydrogen sensor according to the first deformation example of the gas sensor degradation diagnosis device of the embodiments.
Figure 12:
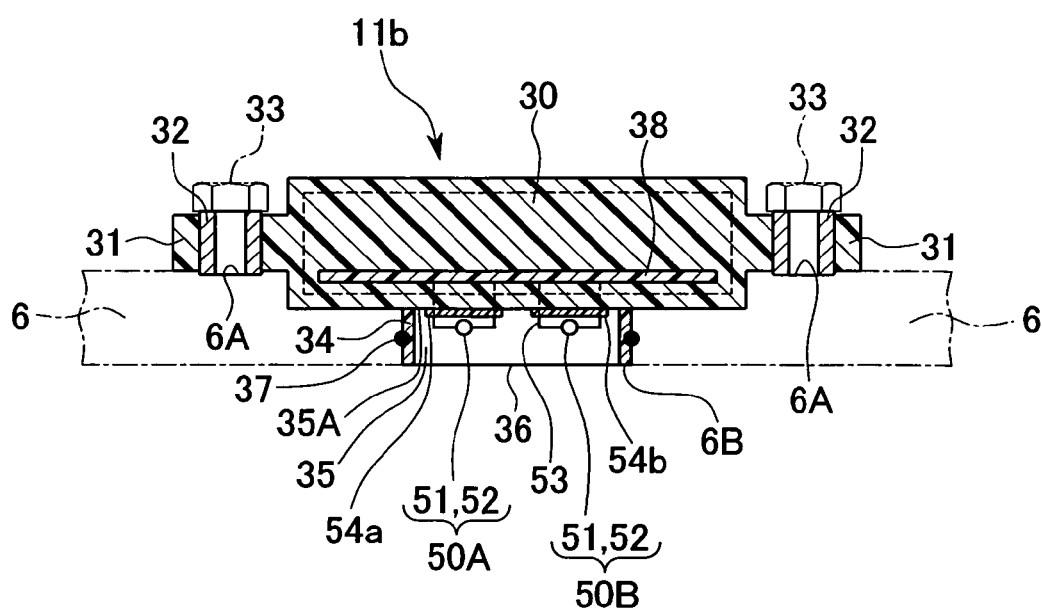
FIG. 12 is a schematic sectional view along line I-I shown in FIG. 11.

In the aforementioned embodiment, the reference detector member 50A and the common detector member 50B are disposed on the same base 54 in the gas detection chamber 35, but it is not limited thereto. As with the hydrogen gas sensors 11a and 11b according to the first modification of the gas sensor degradation diagnosis device 10 in the present mode of operation shown for example in FIG. 11 and FIG. 12, each detector member 50A and 50B may be disposed to be mutually independent on the two different bases 54a and 54b arranged in close proximity so as to be adjacent on the bottom face 35A of the gas detection chamber 35.

Figure 13:
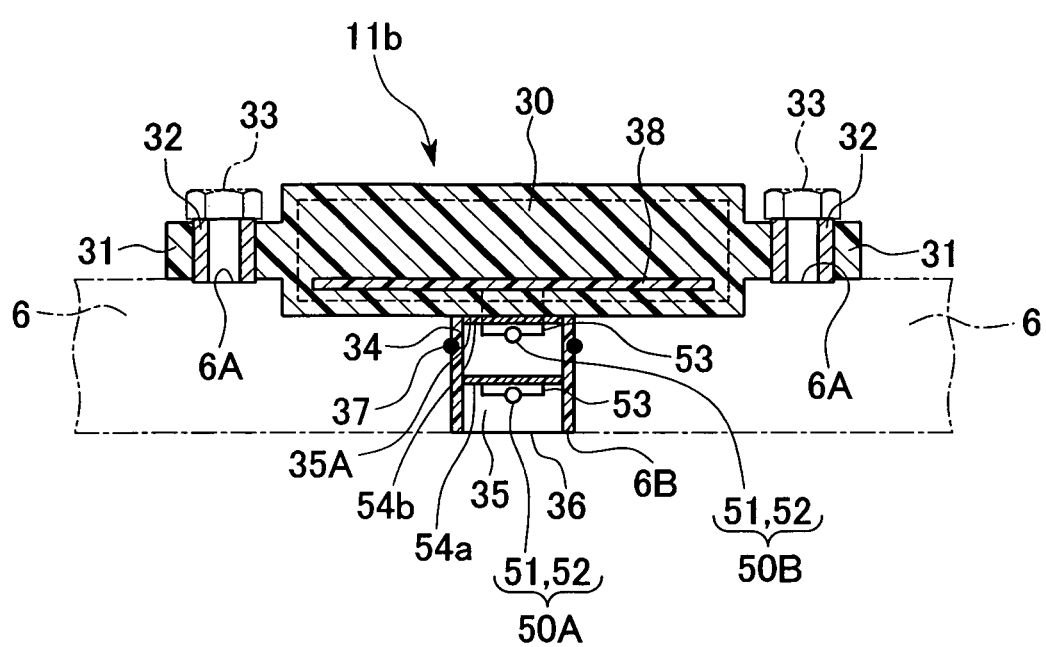
FIG. 13 is a sectional view of the hydrogen sensor according to the second deformation example of the gas sensor degradation diagnosis device of the embodiments.
Figure 14:
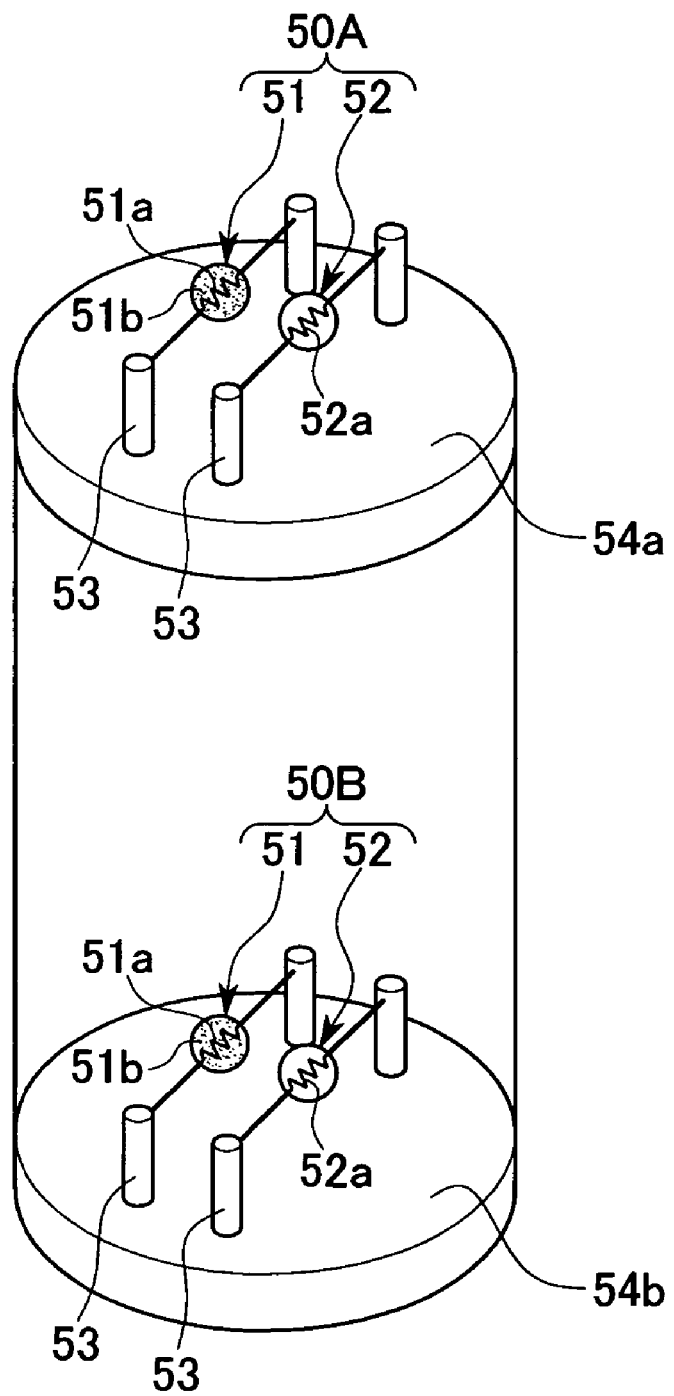
FIG. 14 is a perspective view of the main parts of the hydrogen sensor shown in FIG. 13.

Also, as with the hydrogen gas sensors 11a and 11b according to the second modification of the gas sensor degradation diagnosis device 10 in the present mode of operation shown for example in FIG. 13 and FIG. 14, each detector member 50A and 50B may be disposed to be mutually independent on the two different bases 54a and 54b arranged in close proximity in the gas detection chamber 35 along the thickness direction of each hydrogen sensor 11a and 11b.

Figure 15:
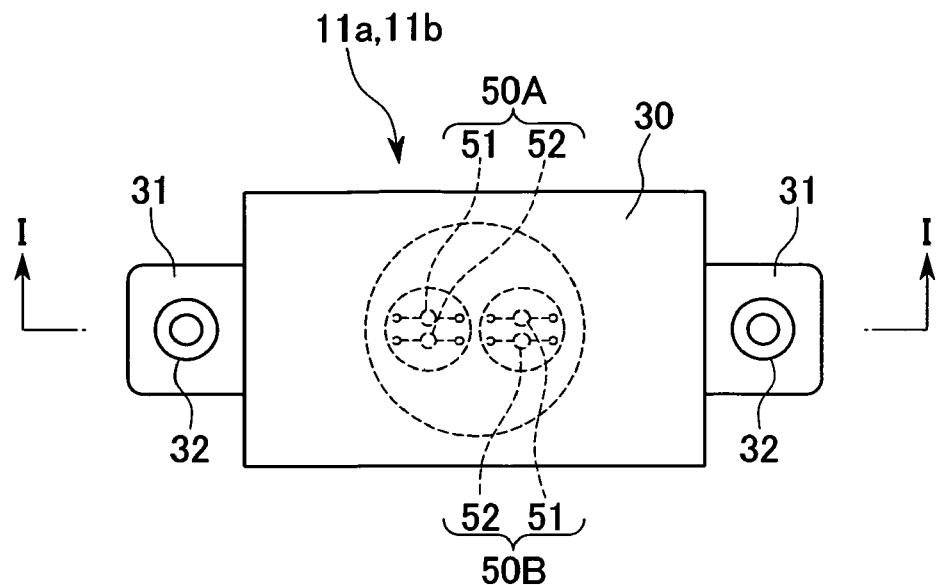
FIG. 15 is a section view of the hydrogen sensor according to the third deformation example of the gas sensor degradation diagnosis device of the embodiments.
Figure 16:
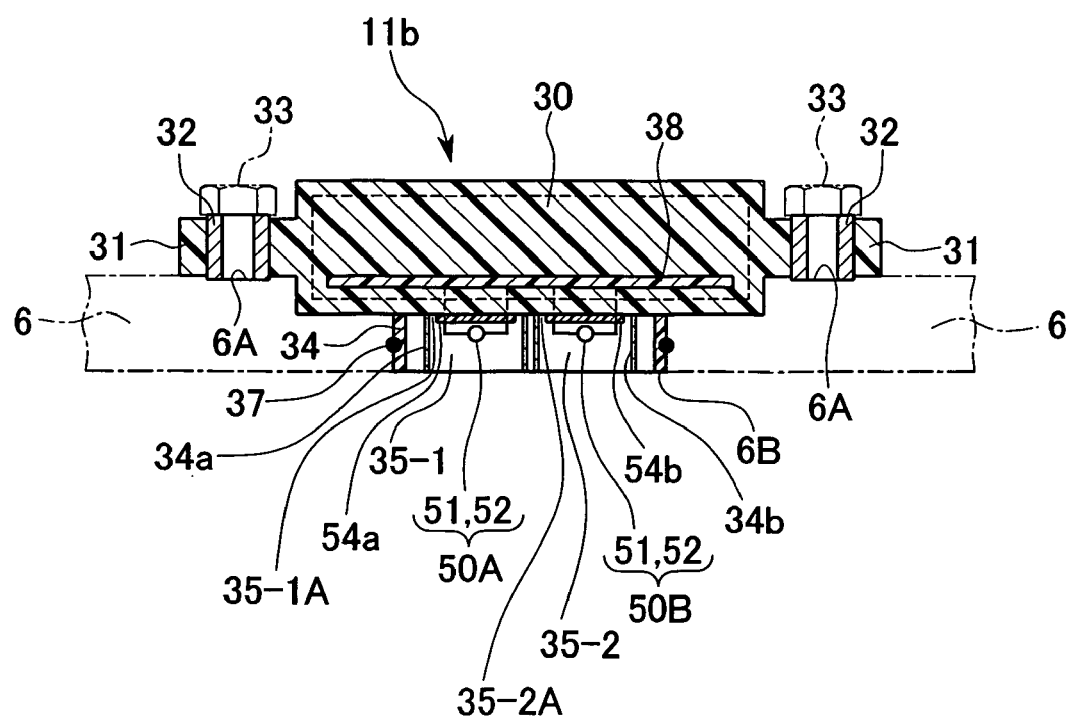
FIG. 16 is a schematic sectional view along line I-I shown in FIG. 15.

Furthermore, in the aforementioned present mode of operation, as with the hydrogen gas sensors 11a and 11b according to the third modification of the gas sensor degradation diagnosis device 10 in the present mode of operation shown for example in FIG. 15 and FIG. 16, a plurality of tubes mutually independent are formed in the tube 34, for example the two of a first tube 34a and second tube 34b, and the first tube 34a may serve as first gas detection chamber 35-a and the second tube 34b may serve as second gas detection chamber 35-2.

In this case, for example the reference detector member 50A is disposed on the first base 54a arranged on the bottom face 35-1A of the first gas detection chamber 35-1, and the common detector member 50B is disposed on the second base 54b arranged on the bottom face 35-2A of the second gas detection chamber 35-2.

Figure 17:
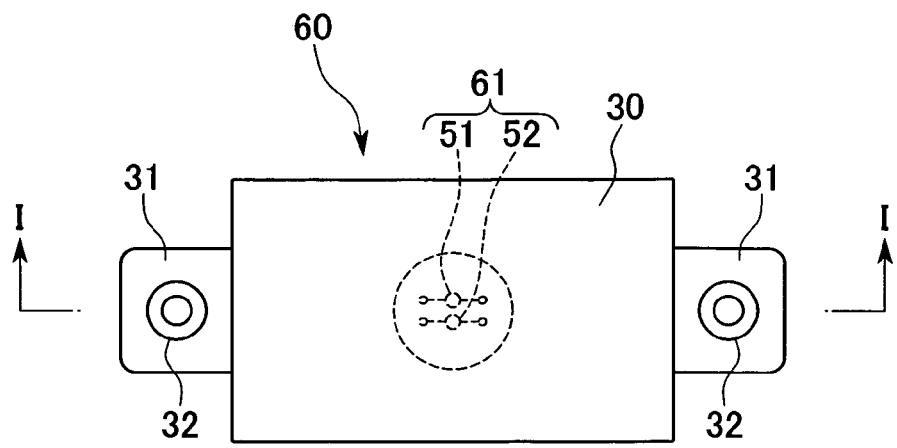
FIG. 17 is a section view of the hydrogen sensor according to the fourth deformation example of the gas sensor degradation diagnosis device of the embodiments.
Figure 18:
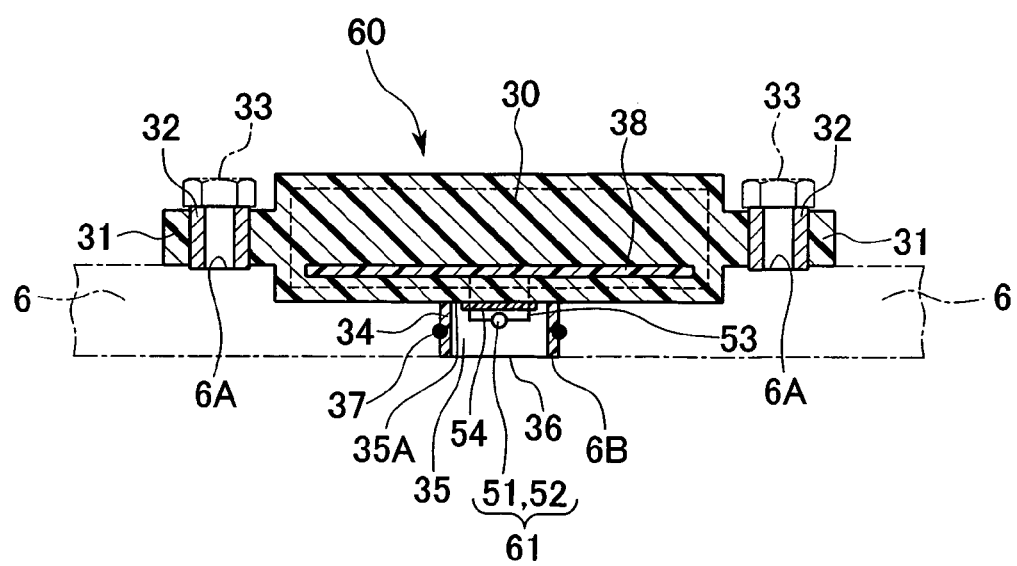
FIG. 18 is a schematic sectional view along line I-I shown in FIG. 17.

Furthermore, in the aforementioned present mode of operation, the reference detector member 50A and common detector member 50B were disposed in the gas detection chamber 35 of each hydrogen sensor 11a and 11b, but it is not limited thereto. As with the hydrogen sensor 60 according to the fourth modification of the gas sensor degradation diagnosis device 10 in the present mode of operation shown for example in FIG. 17 and FIG. 18, the hydrogen sensor 60 having a set of detector members 61 inside the tube 34 is provided in plurality, and each detector member 61 of the plurality of hydrogen sensors 60 may be made to correspond to the reference detector member 50A or common detector member 50B. In the hydrogen sensor 60 according to this fourth modification, the set of detector members 61 is constituted with detector element 51 and temperature compensation element 52 forming a pair. In the hydrogen sensor 60, the same reference numerals are used for the same portions as the aforementioned mode of operation, so their explanation will be omitted.

Figure 19:
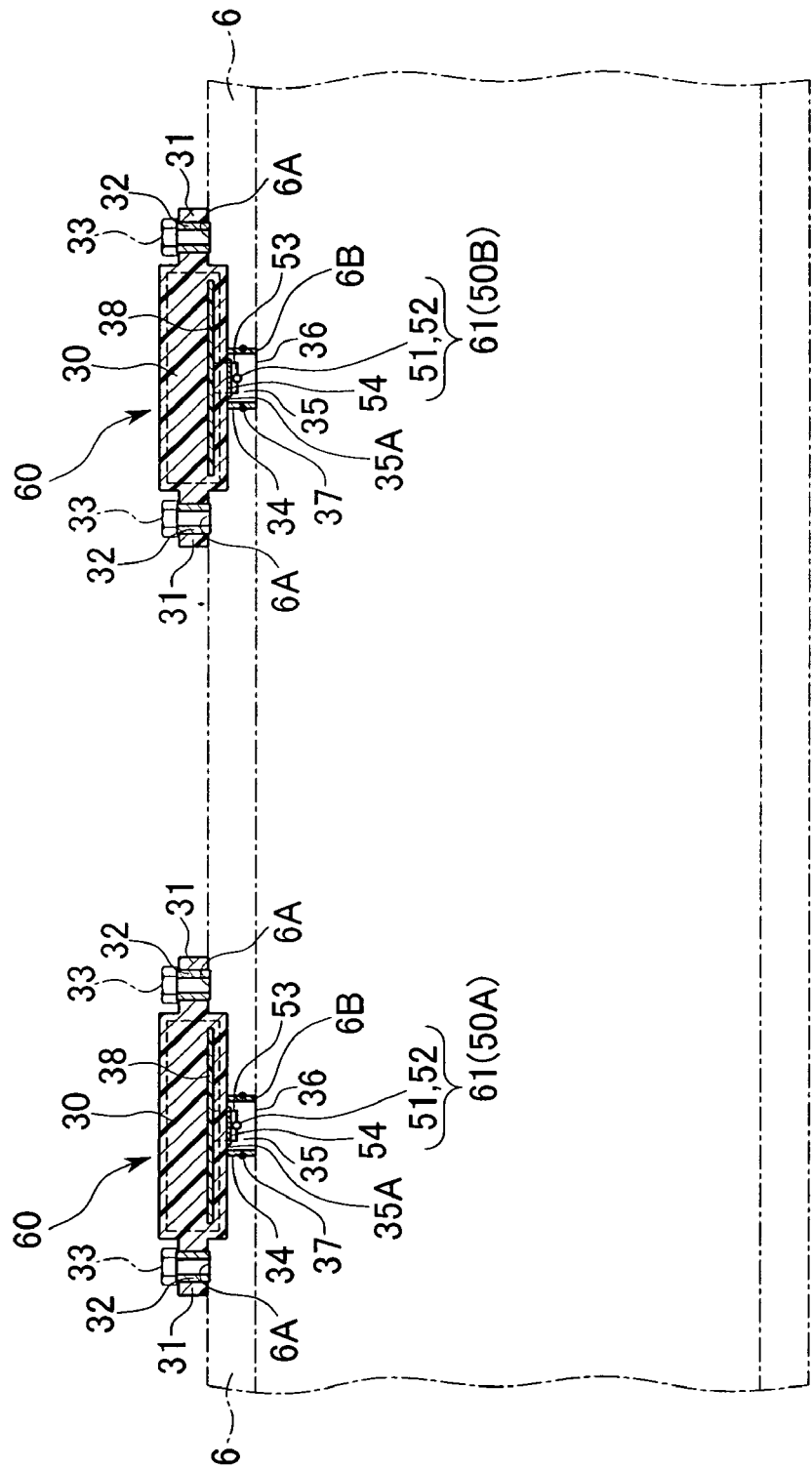
FIG. 19 is sectional view parallel to the axis of the outlet side conduit showing an example of the arrangement position at the outlet side conduit of the oxygen terminal side of the hydrogen sensor shown in FIG. 17.

As shown for example in FIG. 19, in the outlet side conduit 6 of the oxygen terminal side, in the lengthwise direction of this outlet side conduit 6, a plurality, for example two hydrogen sensors 60 and 60 are disposed in close proximity so as to be adjacent. The detector member 61 of one hydrogen sensor 60 serves as the reference detector member 50A, and the detector member 61 of the other hydrogen sensor 60 serves as the common detector member 50B.

Figure 20:
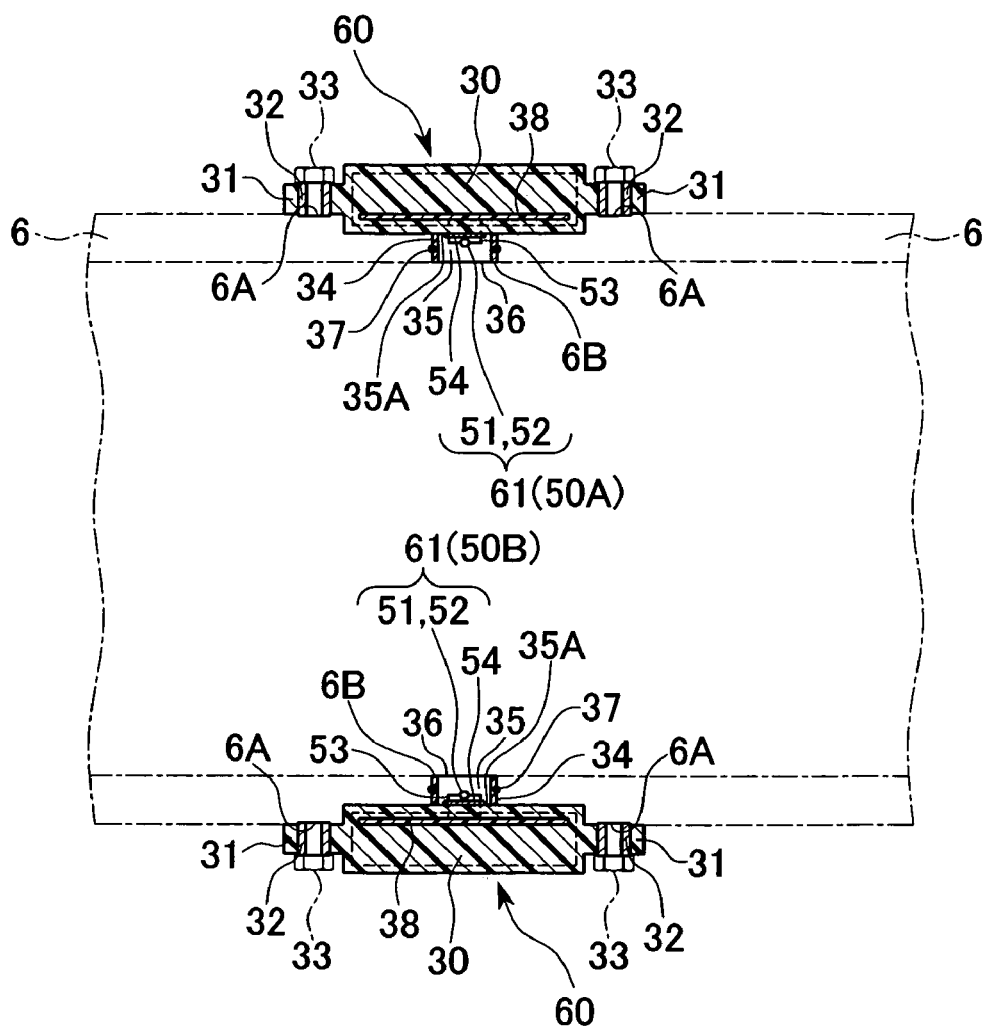
FIG. 20 is sectional view parallel to the axis of the outlet side conduit showing an example of the arrangement position at the outlet side conduit of the oxygen terminal side of the hydrogen sensor shown in FIG. 17.
Figure 21:
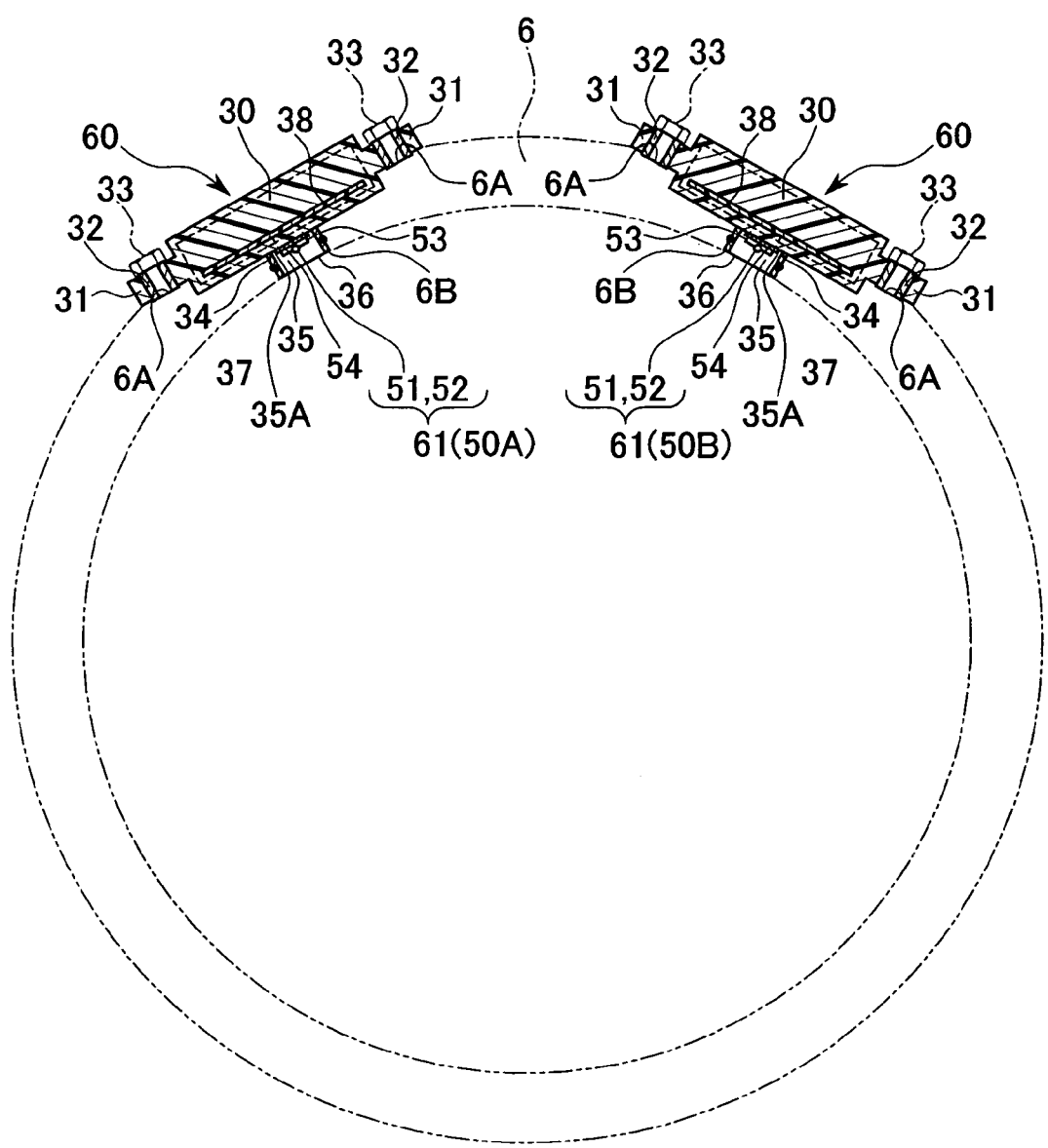
FIG. 21 is a section view perpendicular to the axis of the outlet side conduit showing an example of the arrangement position at the outlet side conduit of the oxygen terminal side of the hydrogen sensor shown in FIG. 17.

In the gas sensor degradation diagnosis device 10 according to the fourth modification of this mode of operation, as shown for example in FIG. 20, a plurality, for example two hydrogen sensors 60 and 60 may be placed opposite each other in the radial direction of the outlet side conduit 6. And as shown for example in FIG. 21, a plurality, for example two hydrogen sensors 60 and 60 may be disposed in close proximity in appropriate positions along the circumference of the outlet side conduit 6.

In the gas sensor degradation diagnosis device 10 according to the fourth modification of the present mode of operation, a plurality of hydrogen sensors 60 may be disposed in close proximity at appropriate positions in the interior of the vehicle 1.

In the aforementioned present mode of operation, each hydrogen sensor 11a and 11b is provided with the two sets of reference detector member 50A and common detector member 50B, but it is not limited thereto, as three or more sets of detector members may also be provided in mutual close proximity. In this case, it is more preferable for the constitution of each hydrogen sensor 11a and 11b to have one set of reference detector member 50A and two or more sets of common detector member 50B 1, 50B2, . . . 50Bn (N is an arbitrary natural number).

Figure 22:
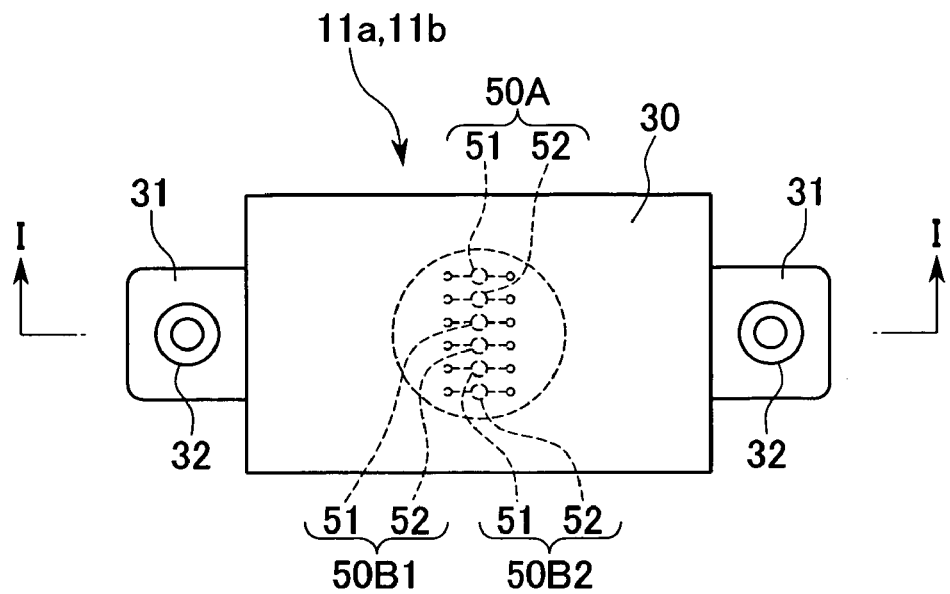
FIG. 22 is a sectional view of the hydrogen sensor according to the fifth deformation example of the gas sensor degradation diagnosis device of the embodiments.
Figure 23:
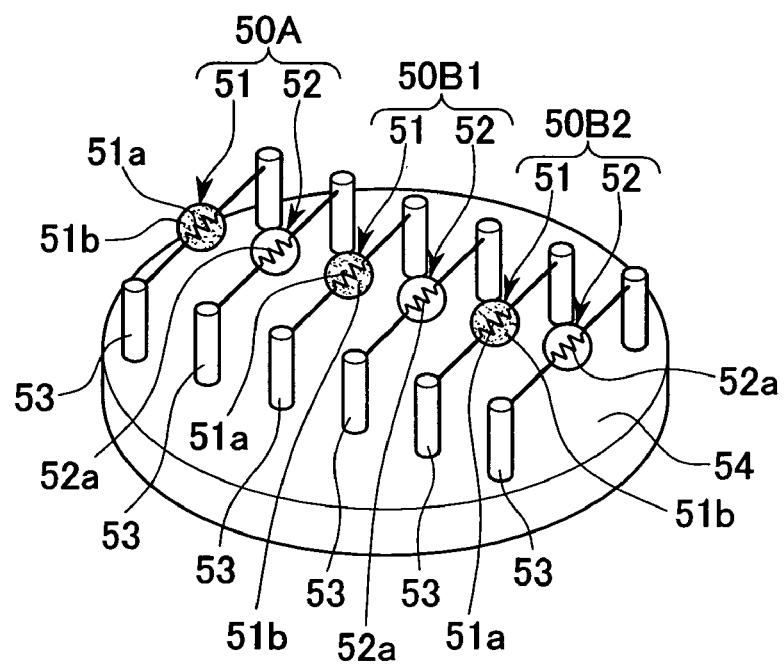
FIG. 23 is a perspective view of the main parts of the hydrogen sensor shown in FIG. 22.

In each hydrogen sensor 11a and 11b according to the fifth modification of the gas sensor degradation diagnosis device 10 of the mode of operation shown in FIG. 22 and FIG. 23, the one set of reference detector member 50A and two sets of common detector members 50B1 and 50B2 are disposed for example on the same base 54 in the gas detection chamber 35, and each detector member 50A, 50B 1, 50B2 is respectively constituted of detector element 51 and temperature compensating element 52 that form a pair. Elements 51 and 52 are arranged so as to form a pair with a prescribed clearance at a position separated by the prescribed distance in the thickness direction of hydrogen sensors 11a and 11b from the base 54 disposed on the bottom face 35A of the gas detection chamber 35 by a plurality of, such as 12, pins 53 connected to the circuit substrate 38.

In this case, the plurality of common detector members 50B1, 50B2, . . . 50Bn in which degradation occurs relatively easier than reference detector member 50A are switchably used in succession corresponding to the degradation date of each common detector member 50B1, 50B2, . . . 50Bn. For example, in the normal operating condition of the vehicle 1 in which generation of electrical energy is being performed in the fuel cell 2, first power is supplied to the first common detector member 50B1 and the hydrogen gas concentration of the gas subject to inspection is detection. When this first common detector member 50B1 is determined to be degraded, power is switched to any of the other common detector members 50B2, . . . 50Bn and the hydrogen gas concentration is detected.

Furthermore, when all the common detector members 50B1, 50B2, . . . 50Bn are determined to have degraded, the setting may be made for detection of the hydrogen gas concentration of the gas subject to inspection to be performed by the reference detector member 50A.

In the aforementioned present mode of operation, the degradation diagnosis section 66 output the diagnosis result, but it is not limited thereto. For example, when each detector member 50A and 50B is determined to be degraded, by outputting the signal of the value outside the range of possible output values from each hydrogen sensor 11a and 11b from the output circuit 68, anomalies of each hydrogen sensor may be notified to devices external to the control device 12 and the like.

In the aforementioned mode of the operation, when performing degradation diagnosis of hydrogen sensors 11a and 11b by relative diagnosis, in a normal operating condition of the vehicle 1 in which generation of electrical energy is being performed in the fuel cell 2, power was simply connected to the reference detector member 50A of hydrogen sensor 11a and 11b (step S01), but is not limited thereto. For example, as in the flowchart in FIG. 24 showing the operation of the gas sensor degradation diagnosis device 10 according to the sixth modification of the present mode of operation, a process may be added to set the hydrogen gas concentration of the gas subject to inspection supplied to each hydrogen sensor 11a and 11b to at least an appropriate value within the detectable range of each hydrogen sensor 11a and 11b.

Figure 24:
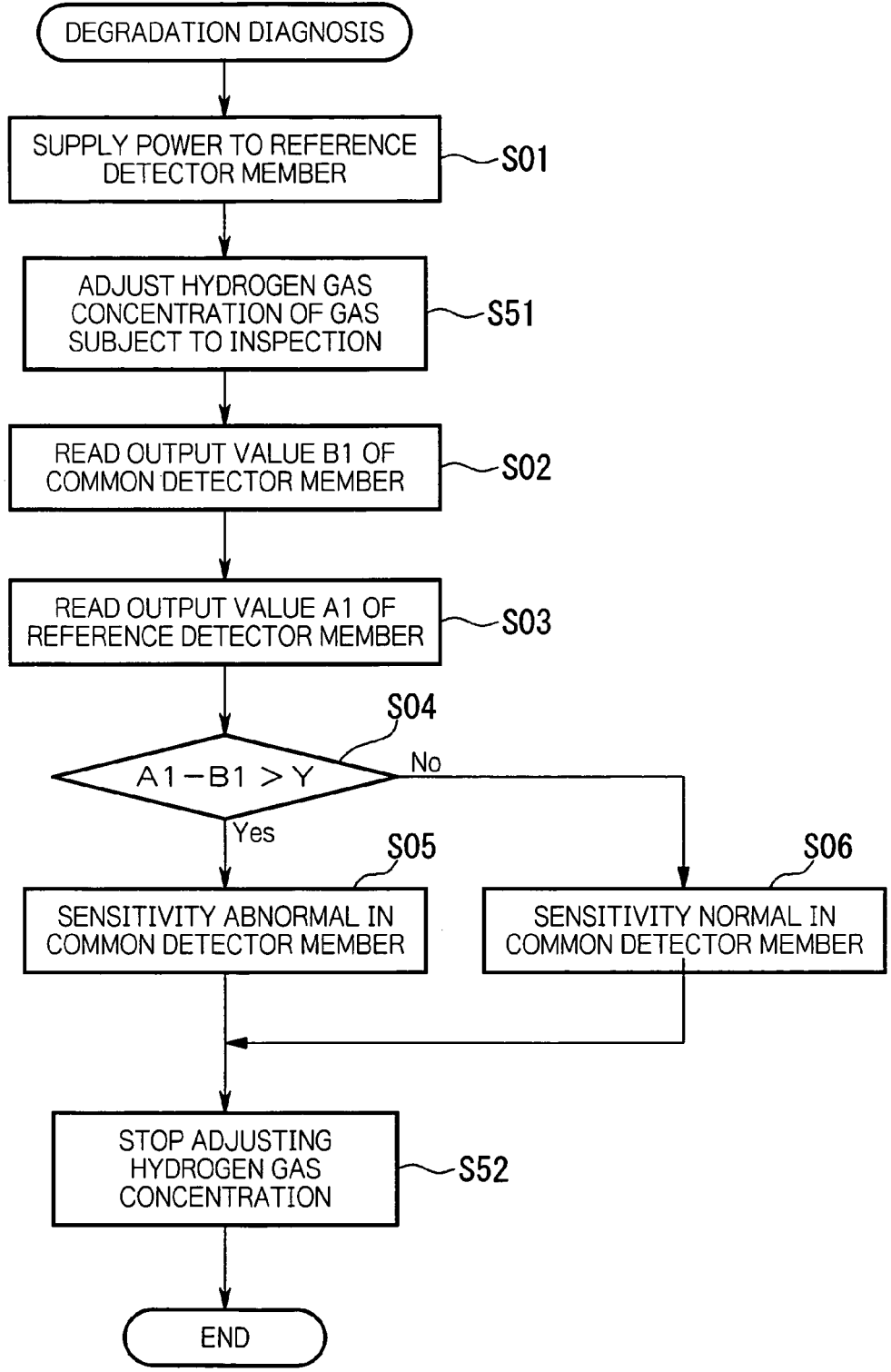
FIG. 24 is a flowchart showing the process of degradation diagnosis by a gas sensor degradation diagnosis method according to the sixth deformation example of the embodiments, particularly relative diagnosis.

For example, in step S01 shown in FIG. 24, power is supplied to the reference detector member 50A of each hydrogen sensor 11a and 11b and then step S51 is proceeded to.

In step S51, the hydrogen gas concentration of the gas subject to inspection is adjusted to an appropriate value within the detectable range of at least each hydrogen sensor 11a and 11b, and then step S02 is proceeded to. For example, with respect to the hydrogen sensor 11b disposed in the outlet side conduit 6 of the oxygen terminal side, by opening the purge valve 24 and the introduction valve 28 in the dilute gas supply device 29, the hydrogen gas concentration in the air off-gas after mixing of the dilute gas is set to the hydrogen gas concentration of the dilute gas so as to be a value within the detectable range of at least hydrogen sensor 11b, and the dilution factor is set by the dilution device 26.

However, here the value of the hydrogen gas concentration of the gas subject to inspection need not be a known value.

In the aforementioned step S05 or step S06, after determining whether or not each hydrogen sensor 11a and 11b is degraded, step S52 shown for example in FIG. 24 is proceeded to, and the process of adjusting the hydrogen gas concentration of the gas subject to inspection begun in the aforementioned step S51 is stopped to end the series of processes.

For example, with regard to the hydrogen sensor 11b disposed on the outlet side conduit 6 of the oxygen terminal side, the purge valve 24 and the introduction valve 28 in the dilute gas supply device 29 are closed.

Figure 25:
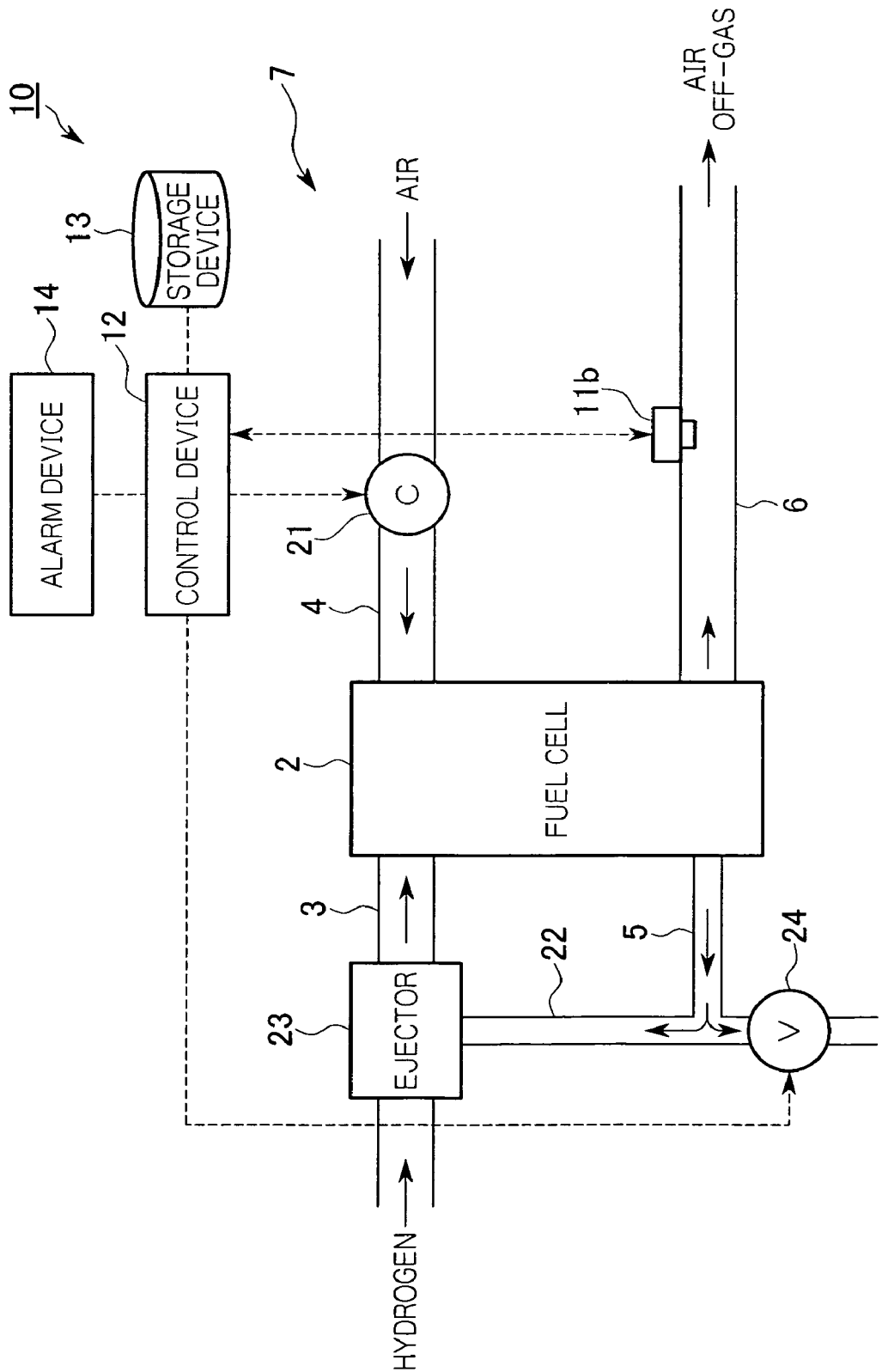
FIG. 25 is a block diagram of the main parts of the fuel cell system having a gas sensor degradation diagnosis device according to the seventh deformation example of the embodiments.

The aforementioned mode of the present operation has a dilute gas supply device 29 constituted by the purge valve 24, hydrogen discharge path 25, dilution device 26, reflux path 27 and introduction valve 28, but is not limited thereto. For example, when executing only degradation diagnosis by relative diagnosis with respect to the each hydrogen sensor 11a and 11b, the hydrogen discharge path 25, dilution device 26, reflux path 27 and introduction valve 28 may be omitted similarly to the seventh modification of the gas sensor degradation diagnosis device 10 of the present mode of operation shown for example in FIG. 25.

Figure 26:
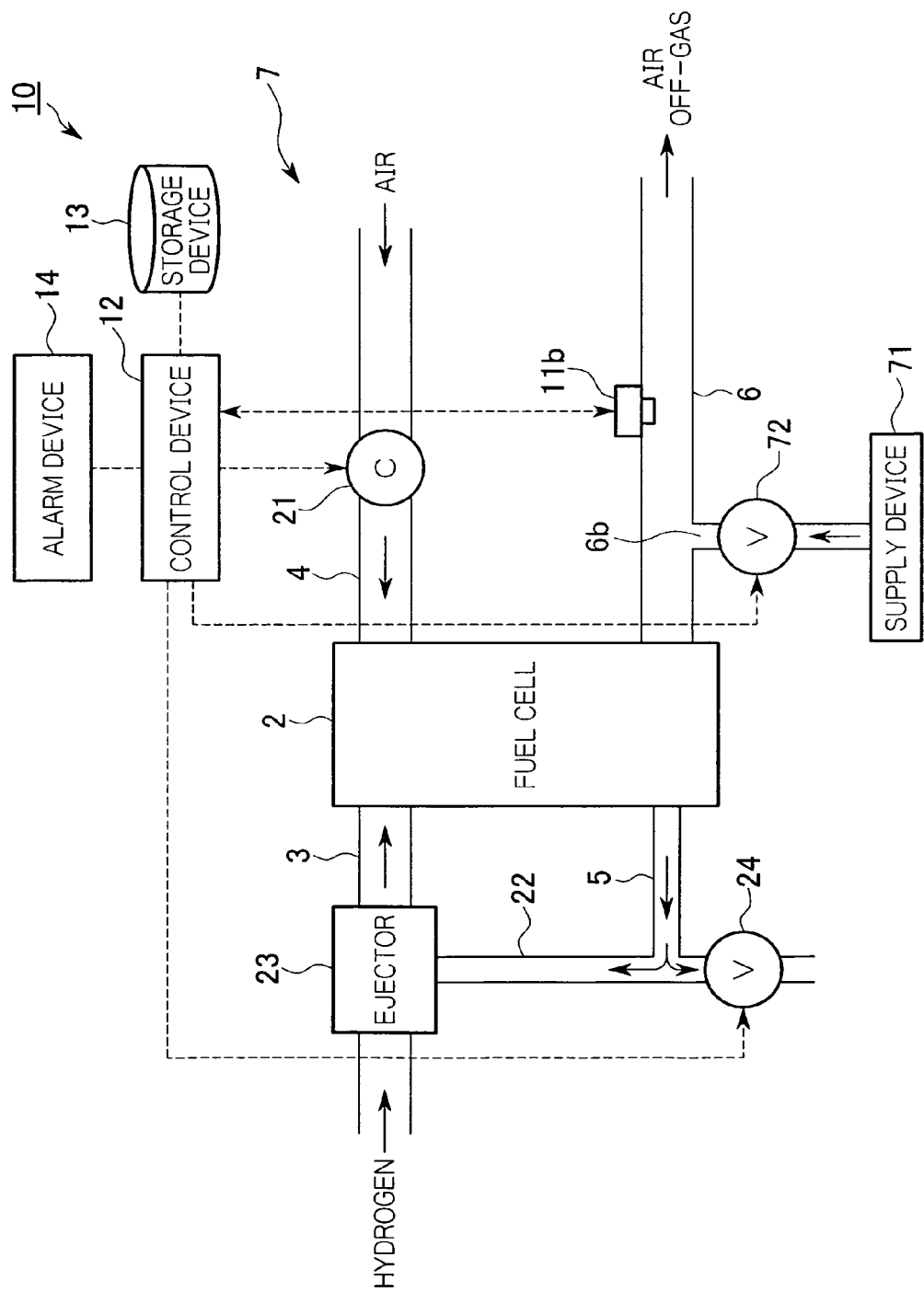
FIG. 26 is a block diagram of the main parts of the fuel cell system having a gas sensor degradation diagnosis device according to the eight deformation example of the embodiments.

Furthermore, like the eighth modification of the gas sensor degradation diagnosis device 10 of the present mode of operation shown for example in FIG. 26, a supply device 71 for supplying a reference gas of an appropriate or prescribed hydrogen gas concentration that is disposed outside the fuel cell system 7 for example may be provided instead of the hydrogen discharge path 25, dilution device 26, reflux path 27 and introduction valve 28 of the dilute gas supply device 29. Here, the reference gas supplied from the supply device 71 is arranged to be introduced to the position 6b (the dilute gas introduction portion) further upstream from the hydrogen sensor 11b in the outlet side conduit 6 of the oxygen terminal side via for example the introduction valve 72.

Figure 27:
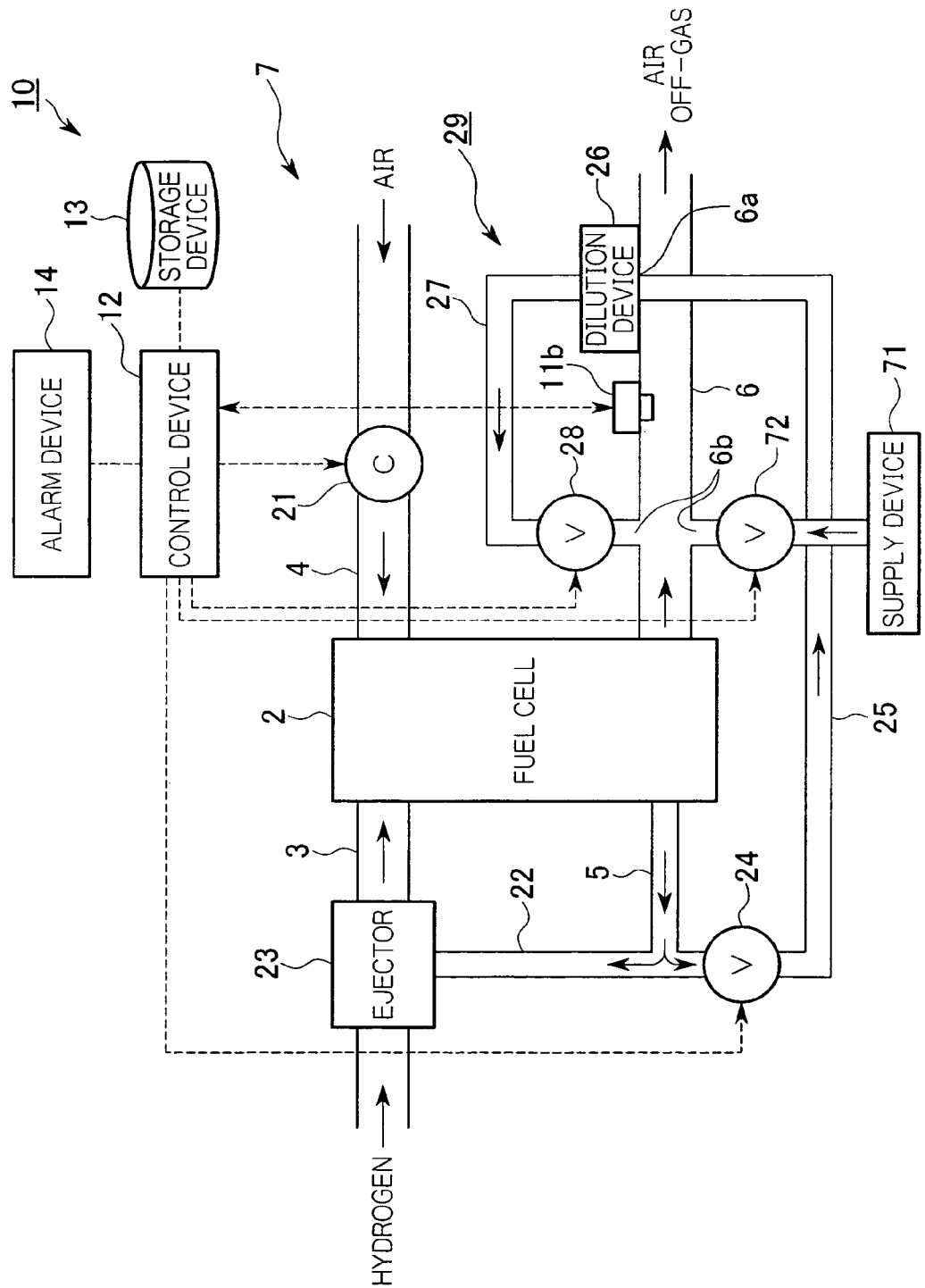
FIG. 27 is a block diagram of the main parts of the fuel cell system having a gas sensor degradation diagnosis device according to the ninth deformation example of the embodiments.

Also, like the ninth modification of the gas sensor degradation diagnosis device 10 of the present operational mode shown for example in FIG. 27, in addition to the dilute gas supply device 29, the supply device 71 and introduction valve 72 may be provided. In this case, the dilute gas supply device 29 and the supply device 71 can be selectively operated according to the diagnosis result of the degradation diagnosis, the condition of the fuel cell system 7, and the condition of the vehicle 1 and the like.

The aforementioned present operational mode has the circuit made by connecting each detector 51 and 52 serves as a bridge circuit, but it not limited thereto. For example, it may also be another circuit such as a series circuit. And the detection value of the voltage or current between prescribed contacts may be output to the control device 12 as a state quantity related to the resistance value R4 of detector element 51.

In the aforementioned present operational mode, degradation diagnosis is performed by using the difference between the output values of the common detector member 50B and the output values of the reference detector member 50A as the comparison value, but it is not limited thereto. For example, degradation diagnosis may be performed by using the quotient obtained by dividing either one of the output value of the common detector member 50B and output value of the reference detector member 50A by the other as the comparison value.

In the aforementioned present operational mode, relative diagnosis determined whether or not the difference between the output value B1 of the common detector member 50B and the output value of the reference detector member 50A (A1−B1) exceeds the relative prescribed value Y set as the prescribed percentage with respect to output value A1 or output value B1, as shown in step S04 for example, but it is not limited thereto, as an absolute prescribed value (for example, an appropriate value of response or concentration) may also be used instead of the relative prescribed value Y.

Furthermore, the magnitude of the determination threshold value (the aforementioned relative prescribed value Y or absolute prescribed value, etc.) may be altered in accordance with the sign of the difference between the output value B1 of the common detector member 50B and the output value of the reference detector member 50A (A1−B1). For example, when the sign of the difference (A1−B1) is positive, compared to when negative, by setting the determination threshold value lower so that it more easily exceeds the determination threshold value, excessively small evaluation of the concentration of the hydrogen gas that is the gas under detection can be restricted.

Figure 28:
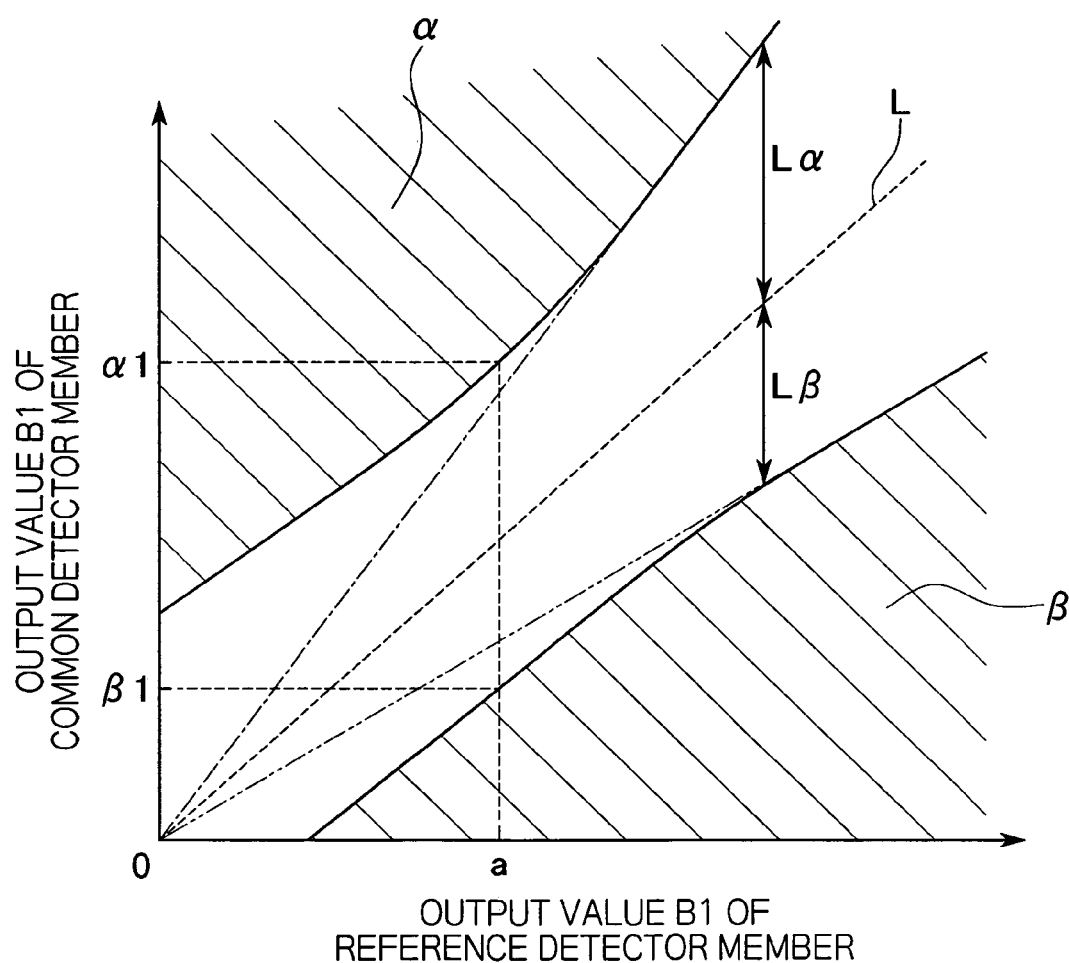
FIG. 28 is a graph showing the degradation determination region corresponding to output value A1 of the reference detector members and output values B1 of the common detector members.

As shown for example in FIG. 28, the prescribed degradation determination region is set in advance according to the output value A1 of the reference detector member 50A and the output value B1 of the common detector member 50B, and a determination is made as to whether or not the output value B1 of the common detector member 50B is within the degradation determination region.

In for example FIG. 28, an excessively large sensitivity degradation region a, in which the output value of common detector member 50B is determined to be excessively large with respect to the reference detector member 50A, and an excessively small sensitivity degradation region β, in which the output value of common detector member 50B is determined to be excessively small, are set. When the output value A1 of reference detector member 50A is for example some value a, determination is made as to whether or not the output value B1 of common detector member 50B is equal to or more than the minimum value α1 of the excessively large sensitivity degradation region α, or the output value B1 of the common detector member 50B is equal to or less than the maximum value β1 of the excessively small sensitivity degradation region β.

Figure 29:
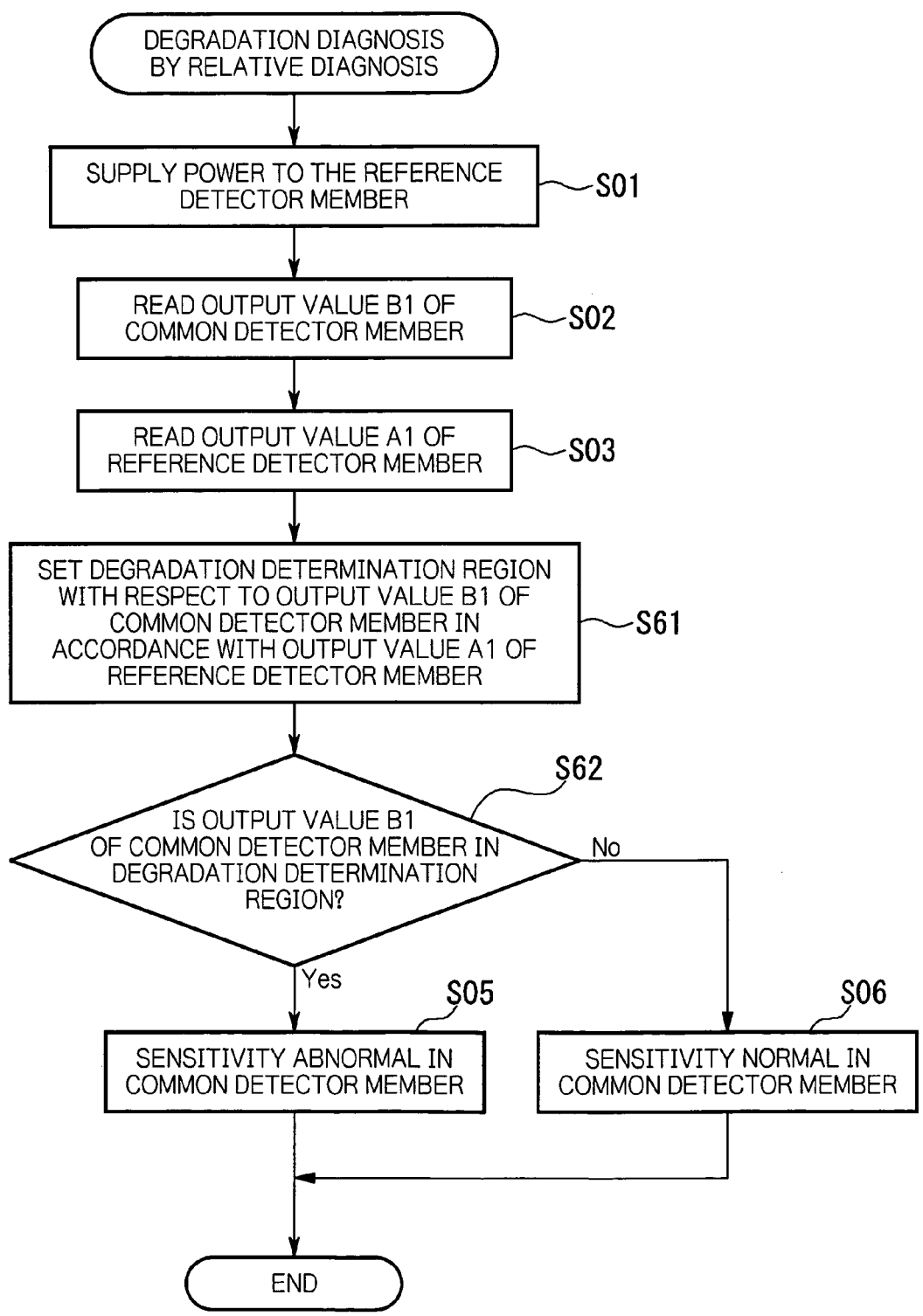
FIG. 29 is a flowchart showing the process of degradation diagnosis by a gas sensor degradation diagnosis method according to the tenth deformation example of the embodiments, particularly relative diagnosis.

In other words, as in the flowchart in FIG. 29 showing the operation of the gas sensor degradation diagnosis method according to the tenth modification of the present operational mode, for example in place of the aforementioned step S04, first in step S61, for example similarly to the graph shown in FIG. 28, the degradation determination region is set with respect to the output value of the common detector member 50B according to the output value A1 of the reference detector member 50A.

Then, in step S62, it is determined whether or not the output value B1 of common detector member 50B is within the degradation determination region. Here, it may be determined whether or not the output value B1 of the common detector member 50B is equal to or more than the minimum value α1 of the excessively large sensitivity degradation region α, or the output value B1 of the common detector member 50B is equal to or less than the maximum value β1 of the excessively small sensitivity degradation region β. And it may be determined whether or not for example the difference (A1–B1) between the output value B1 of the common detector member 50B and the output value A1 of the reference detector member 50A is equal to or less than (A1–α1), or equal to or more than (A1–β1).

When the determination result is "YES", step S05 is proceeded to, and when the determination result is "NO", step S06 is proceeded to.

In the tenth modification of the present operational mode, when setting the degradation determination region such as shown in for example in FIG. 28, it may be set to correspond to the sensitivity dispersion of the reference detector member 50A and the common detector member 50B, that is, the solid difference of each detector member 50A and 50B, degradation condition such as the aged degradation of each detector element 50A and 50B, and the detection accuracy of each detector member 50A and 50B in the initial state of no degradation.

Furthermore, when setting the degradation determination region, compared to the case of the output value of the common detector member 50B being determined to be excessively large as the output value A1 of the reference detector member 50A increases, the output value of the common detector member 50B may be set to be easily determined to be excessively small. That is, as for example shown in FIG. 28, with respect to the straight line L along which the output value A1 of the reference detector member 50A and the output value B1 of the common detector member 50B are equivalent, compared to the difference Lα between the value of the straight line L at an arbitrary output value A1 of the reference detector member 50A and the minimum value α1 of the excessively large sensitivity degradation region α, the difference Lα between the value of the straight line L at an arbitrary output value A1 of the reference detector member 50A and the maximum value β of the excessively small sensitivity degradation region β is set to be less.

In this case, with respect to the actual concentration of the hydrogen gas that is the gas under detection, by expanding the excessively small sensitivity degradation region β in which a lower concentration detection value is obtained with the increase in the output value A1 of the reference detector member 50A, excessively small assessment of the hydrogen gas concentration can be inhibited, and the hydrogen gas exceeding the prescribed concentration can be definitely detected.

In the tenth modification of the present operational mode, for example, instead of the excessively large sensitivity degradation region α and the excessively small sensitivity degradation region β, a normal region in which the output value B1 of the common detector member 50B is determined to be normal with respect to the output value A1 of the reference detector member 50A may be set, and depending on with whether or not the output value B1 of the common detector member 50B is greater than the maximum value of the normal range corresponding to the output value A1 of the reference detector member 50A or whether the output value B1 of the common detector member 50B is less that the minimum value of the normal region corresponding to the output value A1 of the reference detector member 50A, the setting may be made to determine the presence of a sensitivity abnormality.

Also, in the aforementioned operational mode, as shown for example in step S32 and step S42, when determining whether or not the output value B2 of common detector member 50B or the output value A2 of reference detector member 50A are within the range of prescribed value Y2 to prescribed value Y3 in absolute diagnosis, each prescribed value Y2 and Y3 may be set so that determining each output value A2 and B2 to be equal to or less than Y3 is easier compared to determining each output value A2 and B2 to be equal to or more than Y2.

Doing so can simplify detection of the state of sensitivity reduction of each detector member 50A and 50B in which lower concentration detection values are obtained with respect to the actual concentration of hydrogen gas that is the gas under detection.

In the aforementioned operational mode, the gas under detection is assumed to be hydrogen gas, but is not limited thereto, and may be other gas components. Also, the gas sensor is not limited to hydrogen sensor 11a and 11b and may detect other gas components. In addition, the gas sensor is not limited to the hydrogen sensor 11a attached to the roof 1a of the vehicle 1 and hydrogen sensor 11b attached to the outlet side conduit 6 of the oxygen terminal side of fuel cell 2. The gas sensor is not limited to a gas contact combustion-type hydrogen sensor detector, and may be for example a gas heat transfer hydrogen sensor that detects hydrogen using the heat conductivity of each gas contained in the gas subject to inspection, or a non-catalytic-type hydrogen sensor such as an ultrasonic hydrogen sensor.

As set forth above, the gas sensor degradation diagnosis method of the present invention can easily diagnose whether or not a common detector member is degraded or not.

According to the gas sensor degradation diagnosis method of the present invention, when for example feeding gas under detection of an equivalent gas concentration to a plurality of detector members, even if the detection result of each detector member differs in accordance with the arrangement position of each detector member, a lowering of the diagnostic accuracy of the degradation diagnosis of the common detector members by relative diagnosis can be restricted.

Furthermore, according to the gas sensor degradation diagnosis method of the present invention, degradation diagnosis is possible even if the hydrogen gas concentration of the gas subject to inspection during degradation diagnosis is not constant but fluctuating.

Furthermore, according to the gas sensor degradation diagnosis method of the present invention, it can be easily and definitely determined whether or not a common detector member is degraded or not.

Also, according to the gas sensor degradation diagnosis method of the present invention, degradation diagnosis of the reference detector member serving as a reference when relatively diagnosing the degradation diagnosis of the common detector member can be, so to speak, absolutely diagnosed by the output value of the reference detector member, thereby enhancing the diagnostic accuracy of the degradation diagnosis of the common detector member by relative diagnosis.

According to the gas sensor degradation diagnosis method of the present invention, degradation diagnosis of the reference detector members can be carried out by effective utilization of the fuel gas output from the fuel cell.

According to the gas sensor degradation diagnosis method of the present invention, degradation diagnosis can be easily performed with the reference detector members in the mounted state without, for example, removing the reference detector members from the mounted position.

According to the gas sensor degradation diagnosis method of the present invention, by restricting increases in the frequency of supplying power to the reference detector members, degradation of the reference detector members is inhibited and reductions in the diagnostic accuracy of the degradation diagnosis of the common detector members by relative diagnosis can be restricted.

According to the gas sensor degradation diagnosis method of the present invention, degradation diagnosis can be easily performed even for degradation of a gas sensor stemming from poisoning of the catalyst of the detector element by a poisoned material.

According to the gas sensor degradation diagnosis method of the present invention, while accurately grasping the operational status of the fuel cell by a hydrogen sensor, degradation diagnosis of the hydrogen sensor can be easily performed even during operation of the fuel cell.

According to the gas sensor degradation diagnosis method of the present invention, while accurately grasping the operational status of the fuel cell mounted in a vehicle, degradation diagnosis of the hydrogen sensor can be easily performed even during operation of the vehicle.

According to the gas sensor degradation diagnosis device of the present invention, diagnosis of whether or not the common detector members are degraded can be easily performed.

According to the gas sensor degradation diagnosis device of the present invention, when for example feeding gas under detection of an equivalent gas concentration to a plurality of detector members, even if the detection result of each detector member differs in accordance with the arrangement position of each detector member, a lowering of the diagnostic accuracy of the degradation diagnosis of the common detector members by relative diagnosis can be restricted.

Also, according to the gas sensor degradation diagnosis device of the present invention, degradation diagnosis of the reference detector member serving as a reference when relatively diagnosing the degradation diagnosis of the common detector member can be, so to speak, absolutely diagnosed by the output value of the reference detector member, thereby enhancing the diagnostic accuracy of the degradation diagnosis of the common detector member by relative diagnosis.

According to the gas sensor degradation diagnosis device of the present invention, degradation diagnosis of the reference detector members can be carried out by effective utilization of the fuel gas output from the fuel cell.

According to the gas sensor degradation diagnosis device of the present invention, degradation diagnosis can be easily performed with the reference detector members in the mounted state without, for example, removing the reference detector members from the mounted position.

According to the gas sensor degradation diagnosis device of the present invention, degradation diagnosis can be easily performed even for degradation of a gas sensor stemming from poisoning of the catalyst of the detector element by a poisoned material.

According to the gas sensor degradation diagnosis device of the present invention, while accurately grasping the operational status of the fuel cell by a hydrogen sensor, degradation diagnosis of the hydrogen sensor can be easily performed even during operation of the fuel cell.

According to the gas sensor degradation diagnosis device of the present invention, while accurately grasping the operational status of the fuel cell mounted in a vehicle, degradation diagnosis of the hydrogen sensor can be easily performed even during operation of the vehicle.

What is claimed is:

1. A gas sensor degradation diagnosis method for diagnosing the degradation of a detection means employing a plurality of detector members that comprise detector elements and temperature compensating elements and that are disposed in close proximity to one another, with at least one of the plurality of detector members serving as a reference detector member, and the others serving as common detector members, the gas sensor degradation diagnosis method comprising the steps of:
   performing concentration detection of the gas under detection by the common detector members by supplying power only to the common detector members during concentration detection of the gas under detection;
   performing concentration detection of the gas under detection by means of each of the detector members by supplying power to both the common detector members and the reference detector members during degradation diagnosis of the common detector members; and
   performing degradation diagnosis of the common detector members by comparing the output values of the common detector members with the output values of the reference detector members.

2. The gas sensor degradation diagnosis method of claim 1, wherein the plurality of detector members are mutually positioned in close proximity so that substantial differences in the concentration detection results for the gas under detection obtained by each detector member are within the prescribed range.

3. The gas sensor degradation diagnosis method of claim 2, wherein the aforementioned prescribed range is set to within ±10% with respect to the detection result.

4. The gas sensor degradation diagnosis method of claim 1, wherein the gas concentration of the gas under detection is set to an arbitrary concentration detectable by at least the common detector members when performing degradation diagnosis of the common detector members.

5. The gas sensor degradation diagnosis method of claim 1, wherein the gas sensor is judged as degraded when the result of comparing the output values of the common detector members with the output values of the reference detector members is outside the prescribe range.

6. The gas sensor degradation diagnosis method of claim 5, wherein the comparison result is the difference between the output values of the common detector members and the output values of the reference detector members, or the ratio of either of the output values of the common detector members and the output values of the reference detector members to the other.

7. The gas sensor degradation diagnosis method of claim 5, wherein the prescribed range is the prescribed region set in advance according to the output values of the common detector members and the output values of the reference detector members, with the gas sensor being judged as degraded when the output values of the common detector members are greater than the maximum values of the prescribed region corresponding to the output values of the reference detector members, or smaller than the minimum values of the prescribed region corresponding to the output values of the reference detector members.

8. The gas sensor degradation diagnosis method of claim 1, wherein the degradation diagnosis of the reference detector members is performed based on the output values of the reference detector members when the gas under detection is detected by the reference detector members.

9. The gas sensor degradation diagnosis method of claim 8, wherein the gas under detection has a known concentration.

10. The gas sensor degradation diagnosis method of claim 9, wherein the dilute gas, which is obtained by diluting the fuel gas discharged from the fuel cell that generates electricity by electrochemical reaction from supplied fuel gas and oxidant gas with the oxidant gas discharged from the fuel cell, is mixed with the oxidant gas discharged from the fuel cell to serve as the gas under detection of the known concentration.

11. The gas sensor degradation diagnosis method of claim 9, wherein the gas under detection of the required concentration is mixed with an ambient gas of the reference detector members to make the gas under detection of the known concentration.

12. The gas sensor degradation diagnosis method of claim 8, wherein degradation diagnosis of the reference detector members is performed at less frequency than the frequency of performing degradation diagnosis of the common detector members.

13. The gas sensor degradation diagnosis method of claim 1, wherein the detection means is a gas contact combustion-type gas sensor that detects the gas concentration of the gas under detection based on the difference in the electrical resistance values between the detector element and the temperature compensating element generated in accordance with the combustion of the gas under detection that comes into contact with the catalyst of the detector element.

14. The gas sensor degradation diagnosis method of claim 1, wherein the gas under detection is hydrogen gas, and the detection means is a hydrogen sensor that detects the hydrogen gas concentration in oxidant gas discharged from the oxygen electrode of a fuel cell.

15. The gas sensor degradation diagnosis method of claim 1, wherein the gas under detection is hydrogen gas, and the detection means is a hydrogen sensor that detects the hydrogen gas concentration of ambient gas in the interior of a vehicle.

16. A gas sensor degradation diagnosis device comprising:
   a detection means employing a plurality of detector members that comprise detector elements and temperature compensating elements and that are disposed in close proximity to one another, with at least one of the plurality of detector members serving as a reference detector member, and the others serving as common detector members;
   a common detection means that performs concentration detection of the gas under detection by the common detector members by supplying power only to the common detector members during concentration detection of the gas under detection;
   a relative diagnosis means that performs concentration detection of the gas under detection by means of each of the detector members by supplying power to both the common detector members and the reference detector members during degradation diagnosis of the common detector members;
   a comparison means that compares the output values of the common detector members with the output values of the reference detector members; and
   an absolute determination means that performs degradation determination of the common detector members based on the comparison result of the comparison means.

17. The gas sensor degradation diagnosis device of claim 16, wherein the plurality of detector members are mutually positioned in close proximity so that substantial differences in the concentration detection results for the gas under detection obtained by each detector member are within the prescribed range.

18. The gas sensor degradation diagnosis device of claim 17, wherein the aforementioned prescribed range is set to within ±10% with respect to the detection result.

19. The gas sensor degradation diagnosis device of claim 16, further comprising:
   an absolute diagnostic means that performs concentration detection of the gas under detection with the reference detector members by supplying power to the reference detector members during degradation diagnosis of the reference detector members; and
   an absolute determination means that performs degradation determination of the reference detector members based on the output values of the reference detector members.

20. The gas sensor degradation diagnosis device of claim 19, further comprising:
   a fuel cell that generates electricity by electrochemical reaction from the supplied fuel gas and oxidant gas, a dilution means that dilutes the fuel gas discharged from the fuel cell with the oxidant gas discharged from the fuel cell; and a known concentration gas supply means that mixes the dilute gas output from the dilution means with the oxidant gas discharged from the fuel cell to produce the gas under detection of a known concentration and supplies it to the reference detector members.

21. The gas sensor degradation diagnosis device of claim 19, further comprising a known concentration gas supply means that mixes the gas under detection of the prescribed concentration in ambient gas of the reference detector members to produce the gas under detection of a known concentration and supplies it to the reference detector members.

22. The gas sensor degradation diagnosis device of claim 16, wherein the detection means is a gas contact combustion-type gas sensor that detects the gas concentration of the gas under detection based on the difference in the electrical resistance values between the detector element and the temperature compensating element generated in accordance with the combustion of the gas under detection that comes into contact with the catalyst of the detector element.

23. The gas sensor degradation diagnosis device of claim 16, wherein the gas under detection is hydrogen gas, and the detection means is a hydrogen sensor, arranged in the flow of oxidant gas discharged from the oxygen electrode of the fuel cell, that detects the hydrogen gas concentration in the oxidant gas flowing in the path.

24. The gas sensor degradation diagnosis device of claim 16, wherein the gas under detection is hydrogen gas, and the detection means is a hydrogen sensor, positioned in the interior of a vehicle, that detects the hydrogen gas concentration of ambient gas in the vehicle interior.

* * * * *